United States Patent
DeLuca et al.

(10) Patent No.: US 7,534,777 B2
(45) Date of Patent: May 19, 2009

(54) DES-C,D ANALOGS OF 1α,25-DIHYDROXY-19-NORVITAMIN D₃

(75) Inventors: Hector F. DeLuca, Deerfield, WI (US); Katarzyna Plonska-Ocypa, Warsaw (PL); Rafal Sicinski, Warsaw (PL); Pawel Grzywacz, Madison, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 73 days.

(21) Appl. No.: 11/512,705

(22) Filed: Aug. 30, 2006

(65) Prior Publication Data

US 2007/0112077 A1 May 17, 2007

Related U.S. Application Data

(60) Provisional application No. 60/712,365, filed on Aug. 30, 2005.

(51) Int. Cl.
*A61K 31/45* (2006.01)
*C07D 401/00* (2006.01)

(52) U.S. Cl. .................. 514/167; 552/653
(58) Field of Classification Search ............... 514/167; 552/653
See application file for complete search history.

(56) References Cited

U.S. PATENT DOCUMENTS

| | | | |
|---|---|---|---|
| 4,666,634 A | 5/1987 | Miyamoto et al. | |
| 5,086,191 A | 2/1992 | DeLuca et al. | |
| 5,536,713 A | 7/1996 | Deluca et al. | |

(Continued)

OTHER PUBLICATIONS

Yamamoto, et al., "Three-Dimensional Modeling of and Ligand Docking to Vitamin D Receptor Ligand Binding Domain," PNAS, Feb. 15, 2000, vol. 97, No. 4, pp. 1467-1472.

(Continued)

*Primary Examiner*—Sabiha N. Qazi
(74) *Attorney, Agent, or Firm*—Foley & Lardner LLP

(57) ABSTRACT

Des-C,D 2-methylene-19-norvitamin $D_3$ analogs are provided including compounds of formula 1, in which $R^1$ is a straight or branched chain alkyl or alkylene group having from 8 to 27 carbons and bearing an $OY^3$ group; and $Y^1$, $Y^2$ and $Y^3$ are independently selected from H or hydroxy-protecting groups. Such compounds may be used in preparing pharmaceutical compositions and are useful in treating a variety of biological conditions.

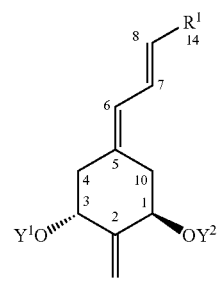

18 Claims, 4 Drawing Sheets

U.S. PATENT DOCUMENTS

| | | | |
|---|---|---|---|
| 5,585,369 | A | 12/1996 | DeLuca et al. |
| 5,843,928 | A | 12/1998 | Deluca et al. |
| 5,936,133 | A | 8/1999 | Deluca et al. |
| 5,945,410 | A | 8/1999 | DeLuca et al. |
| 5,969,190 | A | 10/1999 | Bauer et al. |
| 6,127,559 | A | 10/2000 | DeLuca et al. |
| 6,184,422 | B1 | 2/2001 | Barbier et al. |
| 6,392,071 | B1 | 5/2002 | DeLuca et al. |
| 6,537,981 | B2 | 3/2003 | DeLuca et al. |
| 6,566,352 | B1 | 5/2003 | DeLuca et al. |
| 6,579,861 | B2 | 6/2003 | DeLuca et al. |
| 6,627,622 | B2 | 9/2003 | DeLuca et al. |
| 2004/0220418 | A1 | 11/2004 | DeLuca et al. |

OTHER PUBLICATIONS

Baggiolini, et al., "Stereocontrolled Total Synthesis of 1α,25-Dihydroxycholecalciferol and 1α,25-Dihydroxyergocalciferol," J. Org. Chem. 51, 3098 (1986); published by American Chemical Society.

Daniewski, et al., "A Novel Silylcopper Catalyst for the Reductive Bromination of Hajos Dione. Improved Preparation of a CD Synthon for the Synthesis of Vitamin D," J. Org. Chem. 66, 626-628 (2001); published by American Chemical Society.

Hilpert, et al., "Novel Versatile Approach to an Enantiopure 19-nor, des-C,D Vitamin $D_3$ Derivative," Tetrahedron, 57, 681 (2001); published by Elsevier Science Ltd.

Ono, et al., "Efficient Synthesis of 2-Modified 1α,25-Dihydroxy-19-norvitamin $D_3$ with Julia Olefination: High Potency in Induction of Differentiation on HL-60 Cells," J. Org. Chem., 68, 7407 (2003); published by American Chemical Society.

Yoshida et al., "Efficient and Convergent Coupling Route for the Short-Step Synthesis of Enantiopure 2α-and 2β-Alkylated 1a,25-Dihyrdoxy-19-norvitamin $D_3$ Analogues," Synlett, 8, 1175 (2003); published by Georg Thieme Verlag Stuttgart, New York.

Kutner et al., "Synthesis of Retiferol $RAD_1$ and $RAD_2$, the Lead Representatives of a New Class of des-CD Analogs of Cholecalciferol," Bioorg. Chem., 23, 22 (1995); published by Academic Press, Inc.

Lythgoe, "Synthetic Approaches to Vitamin D and its Relatives," Chem. Soc. Rev. 9, pp. 449-474 (1983).

Lythgoe, et al., "Calciferol and its Relatives. Part 22. A Direct Total Synthesis of Vitamin $D_2$ and Vitamin $D_3$," J. Chem. Soc. Perkin Trans. I, N6, 590 (1978).

Mascareñas, et al., "Studies of the Synthesis of Side-Chain Hydroxylated Metabolites of Vitamin D. 3. Synthesis of 25-Ketovitamin $D_3$ and 25-Hydroxyvitamin $D_3$," J. Org. Chem. 51, 1269 (1986); published by American Chemical Society.

Mincione, et al., "Improved Conversion of Vitamin $D_2$ into the Windaus Ketone and its Regioselective Hydroxylation via Organoboranes at $C_{26}$," Synth. Commun 19, 723 (1989); published by Marcel Dekker, Inc.

Miyamoto, et al., "Synthetic Studies of Vitamin D Analogues. XIV. Synthesis and Calcium Regulating Activity of Vitamin $D_3$ Analogues Bearing a Hydroxyalkoxy Group at the 2β—Position," Chem. Pharm. Bull. 41(6), 1111 (1993); published by Pharmaceutical Society of Japan.

Nishii, et al., "The Development of Vitamin $D_3$ Analogues for the Treatment of Osteoporosis," Osteoporosis Int. Suppl. 1, 190 (1993); published by European Foundation for Osteoporosis.

Okano, et al., "Regulatory Activities of 2β-(3-Hydroxypropoxy)-1α, 25-Dihydroxy-Vitamin $D_3$, a Novel Synthetic Vitamin $D_3$ Derivative, on Calcium Metabolism," Biochem. Biophys. Res. Commun. 163(3), 1444 (1989); published by Academic Press, Inc.

Ostrem et al., "24- and 26-homo-1,25-dihydroxyvitamin $D_3$: Preferential activity in inducing differentiation of human leukemia cells HL-60 in vitro," Proc. Natl. Acad. Sci. USA, 84, 2610 (1987).

Perlman et al., "Novel Synthesis of 19-Nor-Vitamin D Compounds," Tetrahedron Lett. 32(52), 7663 (1991).

Perlman, et al., "1α, 25-Dihydroxy-19-Nor-Vitamin $D_3$, a Novel Vitamin D-related Compound with Potential Therapeutic Activity," Tetrahedron Lett., 31(13), 1823 (1990).

Peterson, et al., "Studies of the Ketone Obtained from the Ozonolysis of Vitamin D. Molecular Mechanics Calculations for It and Related Hydrindanones," J. Org. Chem. 51, 1948 (1986); published by American Chemical Society.

Posner, et al., "2-Fluoroalkyl A-Ring Analogs of 1,25-Dihydroxyvitamin $D_3$-Stereocontrolled Total Synthesis via Intramolecular and Intermolecular Diels-Alder Cycloadditions. Preliminary Biological Testing," J. Org. Chem., 60, 4617 (1995); published by American Chemical Society.

Posner, et al., "Stereocontrolled Total Synthesis of Calcitriol Derivatives: 1,25-Dihydroxy-2-(4'-hydroxybutyl)vitamin $D_3$ Analogs of an Osteoporosis Drug," J. Org. Chem., 59, 7855 (1994); published by American Chemical Society.

Sardina, et al., "Studies on the Synthesis of Side-Chain Hydroxylated Metabolites of Vitamin D. 2. Stereocontrolled Synthesis of 25-Hydroxyvitamin $D_2$," J. Org. Chem. 51, 1264 (1986); published by American Chemical Society.

Sicinski et al., "New Highly Calcemic 1α,25-dihydroxy-19-norvitamin D3 compounds with Modified Side-Chain: 26,27-dihomo- and 26,27-dimethylene analogs in 20S-Series," Steroids, 67, 247 (2002); published by Elsevier Science Inc.

Sicinski, R.R., et al., "New 1α,25-Dihydroxy-19-norvitamin $D_3$ Compounds of High Biological Activity: Synthesis and Biological Evaluation of 2-Hydroxymethyl, 2-Methyl, and 2-Methylene Analogues," J. Med. Chem., 41, 4662-4674 (1998); published by American Chemical Society.

Toh et al., "Studies on a Convergent Route to Side-Chain Analogues of Vitamin D: 25-Hydroxy-23-oxavitamin $D_3$," J. Org. Chem. 48, 1414 (1983); published by American Chemical Society.

DES-C,D ANALOGS OF 1α,25-DIHYDROXY-19-NORVITAMIN D₃

CROSS REFERENCES TO RELATED APPLICATIONS

This application claims priority to U.S. Provisional Application No. 60/712,365, filed Aug. 30, 2005, the entire contents of which are incorporated by reference herein and for all purposes as if fully set forth herein.

FIELD OF THE INVENTION

This invention relates to analogs of vitamin D compounds that do not include the C and D rings, more particularly to des-C, D analogs of 1α,25-dihydroxy-19-norvitamin D₃, and still more particularly to des-C, D analogs of 2-methylene-1α,25-dihydroxy-19-norvitamin D₃ and to pharmaceutical formulations that include these compounds or mixtures thereof. The invention also relates to the use of the compounds, and mixtures thereof in the preparation of medicaments for use in treating various diseases.

BACKGROUND OF THE INVENTION

The natural hormone, 1α,25-dihydroxyvitamin D₃ (also referred to as 1α,25-dihydroxycholecalciferol and calcitriol) and its analog in the ergosterol series, i.e. 1α,25-dihydroxyvitamin D₂ are known to be highly potent regulators of calcium homeostasis in animals and humans, and their activity in cellular differentiation has also been established, Ostrem et al., *Proc. Natl. Acad. Sci.* USA, 84, 2610 (1987). Many structural analogs of these metabolites have been prepared and tested, including 1α-hydroxyvitamin D₃, 1α-hydroxyvitamin D₂, various side chain homologated vitamins, and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies. The structure of 1α,25-dihydroxyvitamin D₃ and the numbering system used to denote the carbon atoms in this compound are shown below.

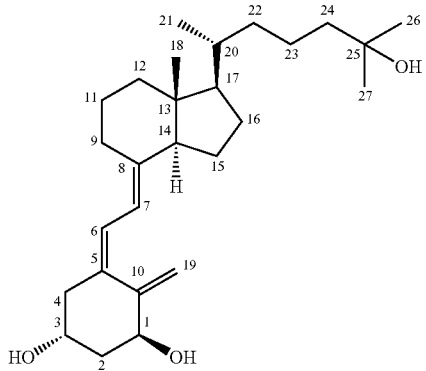

1α,25-Dihydroxyvitamin D₃ =1α,25-Dihydroxycholecalciferol = Calcitriol

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin D₃) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., *Tetrahedron Lett.* 31, 1823 (1990); Perlman et al., *Tetrahedron Lett.* 32, 7663 (1991), and DeLuca et al., U.S. Pat. No. 5,086,191).

Various 2-substituted analogs of 1α,25-dihydroxy-19-norvitamin D₃ have also been synthesized, i.e. compounds substituted at the 2-position with hydroxy or alkoxy groups (DeLuca et al., U.S. Pat. No. 5,536,713), with 2-alkyl groups (DeLuca et a., U.S. Pat. No. 5,945,410), and with 2-alkylidene groups (DeLuca et al., U.S. Pat. No. 5,843,928), which exhibit interesting and selective activity profiles. All these studies indicate that binding sites in vitamin D receptors can accommodate different substituents at C-2 in the synthesized vitamin D analogs.

U.S. Pat. No. 4,666,634 discloses 2β-hydroxy and alkoxy (e.g., ED-71) analogs of 1α,25-dihydroxyvitamin D₃ as potential drugs for use in treating osteoporosis and for use as antitumor agents. See also Okano et al., *Biochem. Biophys. Res. Commun.* 163, 1444 (1989). Other 2-substituted (with hydroxyalkyl, e.g., ED-120, and fluoroalkyl groups) A-ring analogs of 1α,25-dihydroxyvitamin D₃ have been prepared and tested (Miyamoto et al., *Chem. Pharm. Bull.* 41, 1111 (1993); Nishii et al., *Osteoporosis Int. Suppl.* 1, 190 (1993); Posner et al, *J. Org. Chem.* 59, 7855 (1994), and *J. Org. Chem.* 60, 4617 (1995)).

In a continuing effort to explore the 19-nor class of pharmacologically important vitamin D compounds, their analogs which are characterized by the transposition of the ring A exocyclic methylene group from carbon 10 (C-10) to carbon 2 (C-2), i.e. 2-methylene-19-nor-vitamin D compounds have been recently synthesized and tested (Sicinski et al., *J. Med. Chem.*, 41, 4662 (1998); Sicinski et al., *Steroids* 67, 247 (2002); DeLuca et al., U.S. Pat. Nos. 5,843,928, 5,936,133 and 6,382,071). Molecular mechanics studies, performed on these analogs, showed that a change of ring-A conformation can be expected resulting in the "flattening" of the cyclohexanediol ring. From molecular mechanics calculations and NMR studies of these compounds, the A-ring conformational equilibrium was established to be about 6:4 in favor of the conformer that has an equatorial 1α-OH. Introduction of the 2-methylene group into the 19-nor-vitamin D carbon skeleton changes the character of its (1α- and 3β-) A-ring hydroxyl groups; they are both now in the allylic positions, similar to the 1 a-hydroxyl group (important for biological activity) in the natural hormone, 1α,25-(OH)₂D₃. 1α,25-Dihydroxy-2-methylene-19-norvitamin D analogs are characterized by significant biological potency which is enhanced in compounds with the "unnatural" (20S)-configuration.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-Hydroxy-2-methylene-19-nor-pregnacalciferol is described in U.S. Pat. No. 6,566,352 while 1α-hydroxy-2-methylene-19-nor-(20S)-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to the vitamin D receptor and relatively high cell differentiation activity, but little if any calcemic activity as compared to 1α,25- dihydroxyvitamin $D_3$. Their biological activities make these compounds excellent candidates for a variety of pharmaceutical uses, as set forth in the '352, '861 and '622 patents.

An interesting modification of the vitamin D skeleton is removal of its C and D rings. The first compound (retiferol) lacking the C,D-substructure was disclosed by Kutner et al. ten years ago (Kutner et al., *Bioorg. Chem.*, 23, 22 (1995). Several other des-C,D vitamin $D_3$ derivatives, including 19-nor analogs, have been disclosed (Bauer et al., U.S. Pat. No. 5,969,190; Barbier et al., U.S. Pat. No. 6,184,422) and some of them (Ro 65-2299) have been reported to show improved biological activities [Hilpert and Wirz, *Tetrahedron*, 57, 681 (2001)].

SUMMARY OF THE INVENTION

The invention provides compounds that are analogs of 1α,25-dihydroxy-19-norvitamin $D_3$ that lack the C and D rings such as des-C,D analogs of 2-methylene-19-norvitamin $D_3$, pharmaceutical formulations that include the compounds, and the use of these compounds or mixtures thereof in the preparation of medicaments for use in treating various disease states.

Therefore, in one aspect, the invention provides a 2-methylene-19-norvitamin $D_3$ analog that lacks the C and D rings. In some embodiments, the invention provides compounds of formula 1 having the structure shown below:

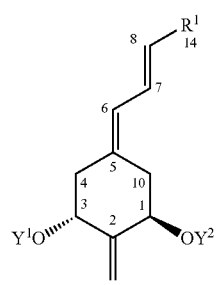

wherein
$R^1$ is a straight or branched chain alkyl or alkylene group having from 8 to 27 carbons and bearing an $OY^3$ group; and
$Y^1$, $Y^2$ and $Y^3$ are independently selected from H or hydroxy-protecting groups.

In some embodiments, the invention provides compounds having the formula 1A, formula 1B, formula 1C, or a mixture thereof as shown below:

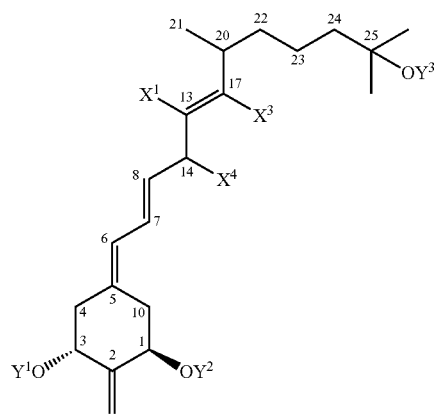

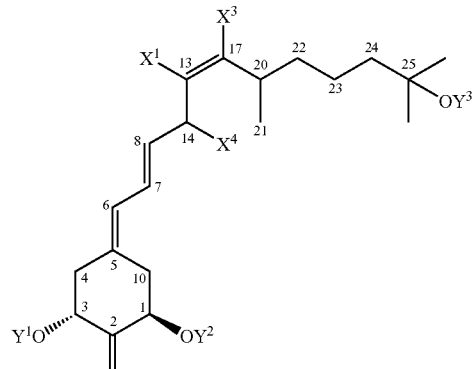

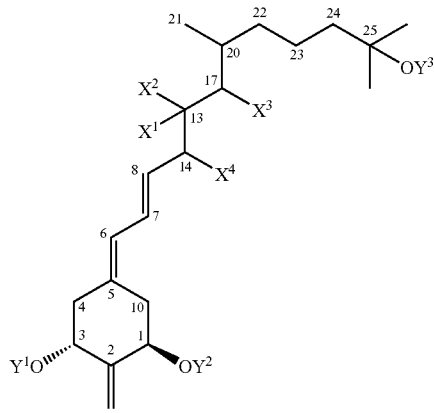

wherein, $X^1$, $X^2$, $X^3$, and $X^4$ are independently selected from H and straight and branched chain alkyl groups having from 1 to 4 carbon atoms including methyl, ethyl, propyl, isopropyl, and butyl groups;

$Y^1$, $Y^2$, and $Y^3$ are independently selected from H or hydroxy-protecting groups;

the carbon atoms at positions 14 and 20 may independently have either the R or S configuration in the compounds of formula 1A and formula 1B; and the carbon atoms at positions 13, 14, 17, and 20 may independently have either the R or S configuration in the compounds of formula 1C.

In some embodiments, $Y^1$ and $Y^2$ are both hydroxy protecting groups such as silyl groups. In some such embodiments, $Y^1$ and $Y^2$ are both t-butyldimethylsilyl groups. In some embodiments, $Y^3$ is a trialkylsilyl group such as a trimethylsilyl or trimethylsilyl group. In other embodiments, $Y^1$, $Y^2$, and $Y^3$ are all H such that the compound has the formula 1A1, 1B1, or 1C1 as shown below. In some such embodiments, each of $X^1$, $X^2$, $X^3$, and $X^4$ is independently selected from H or a methyl group.

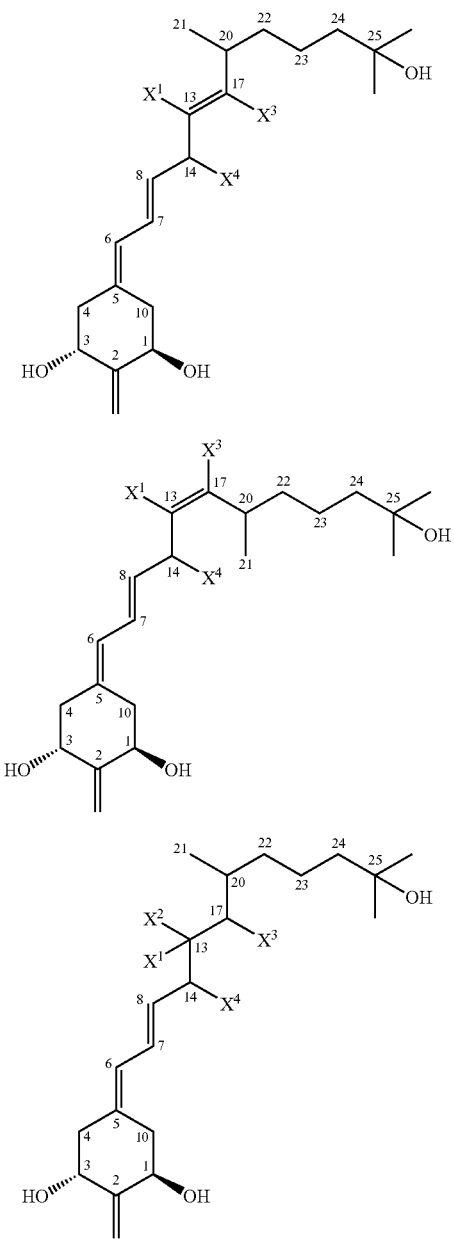
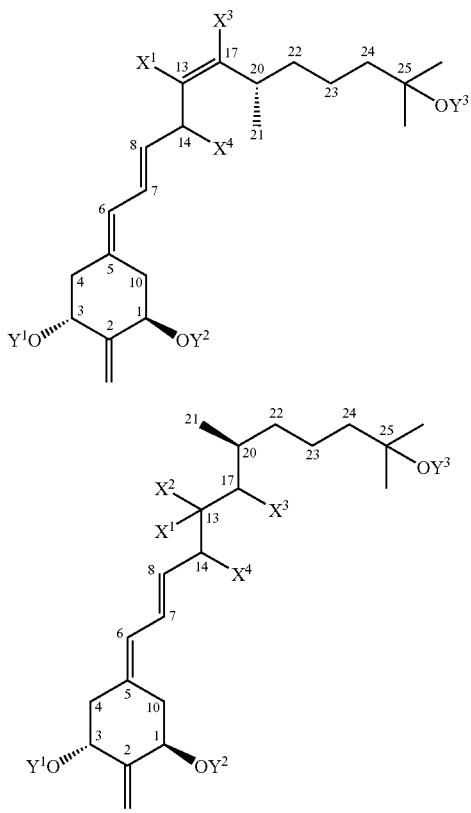

In some embodiments, the compounds of formula 1A, 1B, and 1C have the formula 1A2, 1B2, or 1C2 as shown below:

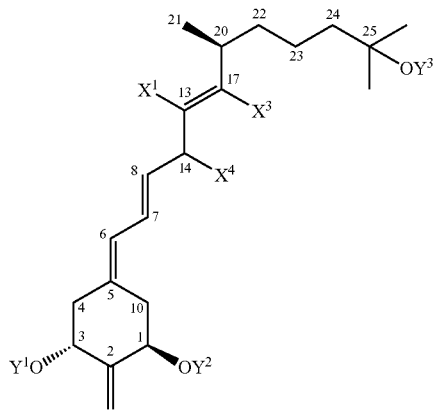

wherein,
$X^1$, $X^2$, $X^3$, and $X^4$ are independently selected from H and straight and branched chin alkyl groups having from 1 to 4 carbon atoms;
$Y^1$, $Y^2$, and $Y^3$ are independently selected from H or hydroxy-protecting groups; the carbon atoms at position 14 have either the R or S configuration in the compounds of formula 1A2 and formula 1B2; and
the carbon atoms at positions 13, 14, and 17 may independently have either the R or S configuration in the compounds of formula 1C2.
In some such embodiments, each of $Y^1$, $Y^2$, and $Y^3$ is H. In some embodiments each of $X^1$, $X^2$, $X^3$, and $X^4$ is independently selected from H or a methyl group.
In some embodiments, the invention provides compounds of formula 1C having the formula 1C3 as shown below:

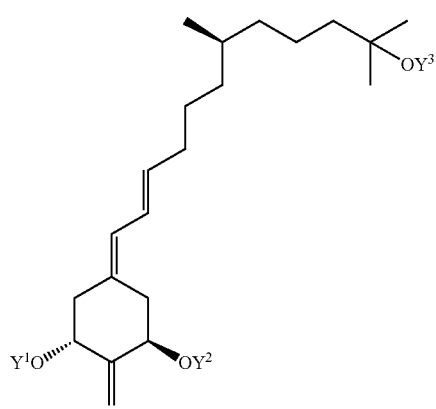

wherein $Y^1$, $Y^2$, and $Y^3$ are independently selected from H or hydroxy-protecting groups. In some such embodiments, $Y^1$, $Y^2$, and $Y^3$ are all hydroxy protecting groups such as silyl groups. In some such embodiments, $Y^1$, and $Y^2$ are t-butyi-dimethylsilyl groups and $Y^3$ is a trialkylsilyl group such as a triethylsilyl group. In other embodiments, $Y^1$, $Y^2$, and $Y^3$ are all H such that the compound has the formula 1C4 as shown below:

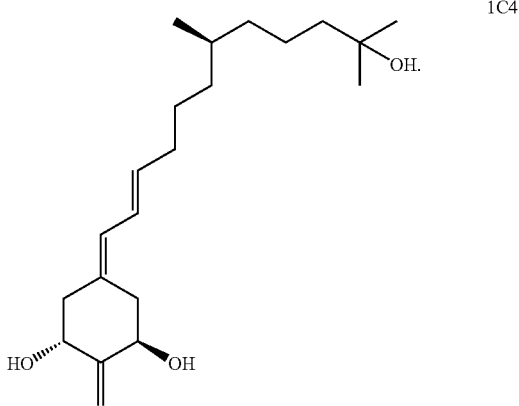

1C4

In some embodiments, the compounds of any of the embodiments may be present in a purified form. In other embodiments, the compounds in a composition may be present as a mixture. In some embodiments, the mixture includes a first compound of the invention and a second compound of the invention, and the ratio of the first compound to the second compound ranges from 50:50 to 99.9:0.1. In some such embodiments, the ratio of the first compound to the second compound ranges from 70:30 to 99.9:0.1, from 80:20 to 99.9:0.1, from 90:10 to 99.9:0.1, or from 95:5 to 99.9:0.1.

The above compounds were/are tested and found to exhibit desired, and highly advantageous, patterns of biological activity with respect to intestinal calcium transport activity, ability to mobilize calcium from bone, and ability to bind to the vitamin D receptor. The compounds may thus find use in treating cancer, skin conditions, and autoimmune disorders. Therefore, in some embodiments, these compounds or pharmaceutical formulations that include one or more compounds of the invention may be employed as therapeutic agents for the treatment of diseases or disorders such as cancer, autoimmune diseases, skin conditions, and secondary hyperparathyroidism. In some embodiments, the treatment may be transdermal, oral, or parenteral.

The compounds of the invention may also be especially suited for treatment and prophylaxis of human disorders which are characterized by an imbalance in the immune system, e.g., in autoimmune diseases, including multiple sclerosis, diabetes mellitus, host versus graft reaction, and rejection of transplants; and additionally, for the treatment of inflammatory diseases, such as rheumatoid arthritis and asthma, as well as the improvement of bone fracture healing and improved bone grafts. Acne, alopecia, skin conditions such as dry skin (lack of dermal hydration), undue skin slackness (insufficient skin firmness), insufficient sebum secretion and wrinkles, and hypertension are other conditions which may be treated with the compounds of the invention.

The compounds described herein were also tested and found to moderate cell differentiation activity. Thus, these compounds may also be used as therapeutic agents for the treatment of psoriasis and/or as anti-cancer agents, especially against leukemia, colon cancer, breast cancer and prostate cancer. In some embodiments, the compounds and compositions of the invention are used to treat a biological condition selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, eczema, or inflammatory bowel diseases; a skin condition selected from wrinkles, lack of adequate skin firmness, lack of adequate dermal hydration, or insufficient sebum secretion; or secondary hyperparathyroidism.

In some embodiments of the methods of the invention, the compound or pharmaceutical composition is administered orally, rectally, parenterally, transdermally, or topically. In other embodiments, the compound or pharmaceutical formulations is administered in an aerosol which may be accomplished using an inhaler or a nebulizer.

The compounds of the invention may be used to prepare pharmaceutical formulations or medicaments that include a compound or a mixture of the compounds of the invention in combination with a pharmaceutically acceptable carrier. Such pharmaceutical formulations and medicaments may be used to treat various biological disorders such as those described herein. Methods for treating such disorders typically include administering an effective amount of the compound, or an appropriate amount of a pharmaceutical formulation or a medicament that includes the compound, to a subject suffering from the biological disorder. "Subject," as used herein, refers to any animal that may experience the beneficial effects of a compound of the invention upon administration of the compound to the animal. In some embodiments, the subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the subject is a primate such as, in some embodiments, a human. In some embodiments, the compounds are used to prepare an aerosol which may include a glycol compound such as propylene glycol.

The compounds may be present in a composition to treat the above-noted diseases and disorders in an amount from about 0.01 µg/gm to about 1 mg/gm of the composition, preferably from about 0.1 µg/gm to about 500 µg/gm of the composition, and may be administered topically, transdermally, orally, rectally, or parenterally in dosages of from about 0.01 µg/day to about 1 mg/day, preferably from about 0.1 µg/day to about 500 µg/day.

Further objects, features and advantages of the invention will be apparent from the following detailed description.

BRIEF DESCRIPTION OF THE DRAWINGS

FIG. 1 is a graph comparing the relative activity of Des-C,D and 1,25(OH)$_2$D$_3$ to compete for binding with [$^3$H]-1,25-(OH)$_2$-D$_3$ to the full-length recombinant rat vitamin D receptor.

FIG. 2 is a graph comparing the percent HL-60 cell differentiation as a function of the concentration of Des-C,D with that of 1,25(OH)$_2$D$_3$.

FIG. 3 is a graph comparing the in vitro transcription activity of Des-C, D with that of 1,25(OH)$_2$D$_3$.

FIG. 4 is a bar graph comparing the bone calcium mobilization activity of Des-C,D with that of 1,25(OH)$_2$D$_3$.

DETAILED DESCRIPTION OF THE INVENTION

Figure 1:
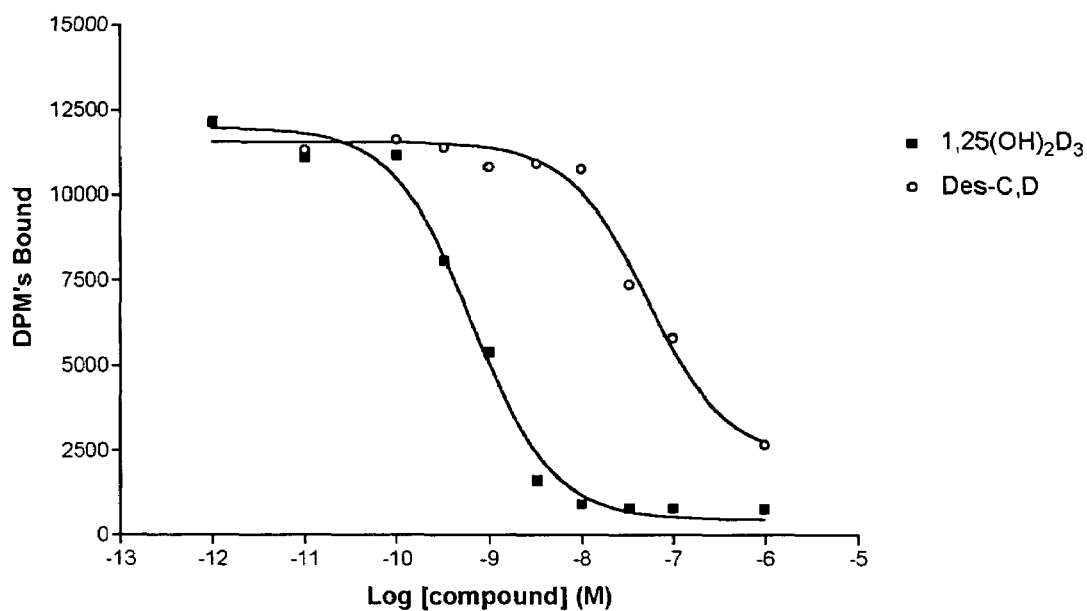
FIGS. 1-4 illustrate various biological activities of the compound of formula 1C4 (referred to as "Des-C,D" in the Figures) compared with those of the native hormone 1α,25-dihydroxyvitamin $D_3$ (referred to as "1,25(OH)$_2$D$_3$" in the Figures).

Generally, the invention provides compounds that are analogs of 1α,25-dihydroxy-19-norvitamin D$_3$ that lack the C and D rings (des-C,D compounds) such as des-C,D analogs of 2-methylene-1α,25-dihydroxy-19-norvitamin D$_3$, pharmaceutical formulations that include the compounds, and the use of these compounds or mixtures thereof in the preparation of medicaments for use in treating various disease states.

In one aspect, the invention provides a 2-methylene-19-norvitamin D$_3$ analog that lacks the C and D rings (a des-C, D-2-methylene-19-norvitamin D$_3$ analog) such as des-C,D-2-methylene-1α,25-dihydroxy-19-norvitamin D$_3$. By 2-methylene-19-norvitamin D$_3$ analog is meant a compound that is an agonist of the vitamin D receptor and at least comprises the 2-methylene-19-norvitamin D$_3$ A ring. In some embodiments, the invention provides compounds of formula 1 having the structure shown below:

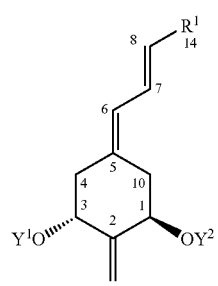

1 wherein,

R$^1$ is a straight or branched chain alkyl or alkylene group having from 8 to 27 carbons and bearing an OY$^3$ group; and Y$^1$, Y$^2$ and independently selected from H or hydroxy-protecting groups.

In some embodiments of the compound of formula 1, R$^1$ is a straight or branched chain alkyl or alkylene group having from 8 to 20 carbons and bearing an OY$^3$ group. In some such embodiments, the alkyl or alkylene group has 8 to 11, 8 to 12 or 8 to 15 carbons.

In some embodiments, the invention provides compounds having the formula 1A, formula 1B, formula 1C, or a mixture thereof as shown below:

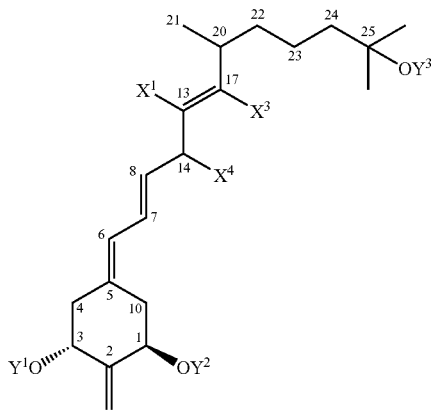

1A

-continued

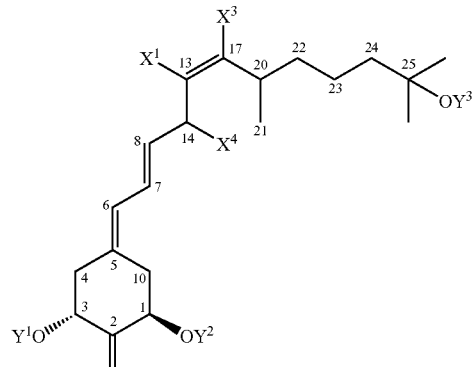

1B

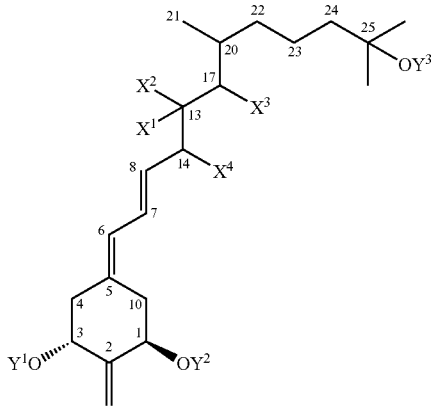

1C wherein,

X1, X2, X3, and X4 are independently selected from H and straight and branched chain alkyl groups having from 1 to 4 carbon atoms including methyl, ethyl, propyl, isopropyl, and butyl groups;

Y$^1$, y2, and y3 are independently selected from H or hydroxy-protecting groups;

the carbon atoms at positions 14 and 20 may independently have either the R or S configuration in the compounds of formula 1A and formula 1B; and the carbon atoms at positions 13, 14, 17, and 20 may independently have either the R or S configuration in the compounds of formula 1C.

As used herein, the phrase "straight and branched chain alkyl groups" refers to groups that include carbon and hydrogen atoms that only include carbon-carbon single bonds and carbon-hydrogen single bonds. Thus, the phrase "straight and branched chain alkyl groups" having 1 to 4 carbon atoms includes alkyl groups such as methyl, ethyl, propyl, i-propyl, and butyl groups.

As used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groups such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

The preparation of des-C,D-19-nor-vitamin D compounds of formula 1A, 1B, and 1C can be accomplished using either of two general methods. In the first method, the Wittig-Horner coupling of an aldehyde (IIa or IIb) with an allylic phosphine oxide (III) is employed. In an alternative procedure, Julia olefination is performed and includes coupling of an unsaturated sulfone (IVa or IVb), easily prepared from the aldehydes IIa or IIb, with the cyclohexanone derivative V. Compounds IIA, IIB, III, IVa, IVb, and V are shown below where the variables have the same meanings as defined above with respect to the compounds of formula 1A, 1B, and 1C, and the wavy lines indicate that both cis and trans isomers are represented in formula IIA and IVA:

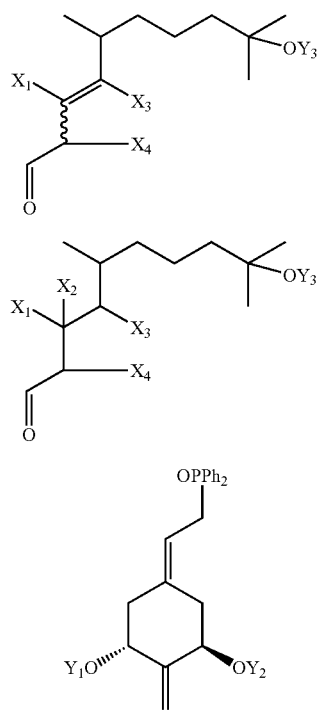

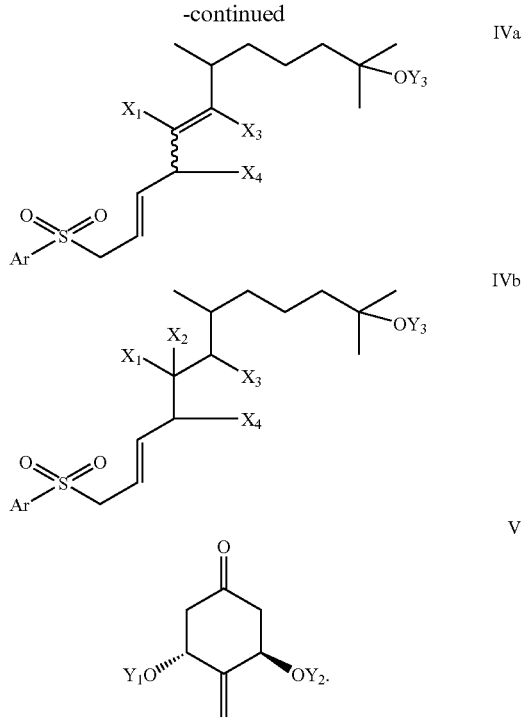

In the structures shown above, Ar represents an aromatic group such as a phenyl, a substituted phenyl, a 2-phenyltetrazolyl, a 2-benzothiazolyl group, and other aromatic groups that are suitable for the Julia olefination process. Those skilled in the art will recognize that any functionalities in the Ar group that might be sensitive to, or interfere with, the condensation reaction, should be avoided. In phosphine oxide III, and cyclohexanone V, $Y_1$ and $Y_2$ are preferably hydroxy-protecting groups such as silyl protecting groups. The t-butyldimethylsilyl (TBDMS) group is an example of a particularly useful hydroxy-protecting group. The general procedures described above represent an application of the convergent synthesis concept, which has been applied effectively for the preparation of vitamin D compounds (e.g. Kittaka et al, Synlett, 8, 1175 (2003), and J. Org. Chem., 68, 7407 (2003).

Phosphine oxide III and cyclohexanone V are convenient reagents that can be used to prepare a large number of 19-nor vitamin D compounds including des-C,D analogs. These compounds may be prepared according to the procedures described by Sicinski et al., J. Med. Chem., 41, 4662 (1998), DeLuca et al., U.S. Pat. No. 5,843,928; Perlman et al., Tetrahedron Lett. 32, 7663 (1991); and DeLuca et al., U.S. Pat. No. 5,086,191. Scheme 1 shows the general procedure for synthesizing phosphine oxide III (See Scheme 1, compound H) and cyclohexanone V (See Scheme 1, compound D) as outlined in U.S. Pat. No. 5,843,928 which is hereby incorporated by reference in its entirety as if fully set forth herein. Modification of the method shown in Scheme 1 may be used to produce a large number of vitamin D analogs as will be apparent to those skilled in the art. For example, a wide variety of phosphonium compounds may be used in place of the $MePh_3P^+Br^-$ used to convert ketone B to alkene C. Examples of such compounds include $EtPh_3P^+Br^-$, $PrPh_3P^+Br^-$, and compounds generally prepared by reaction of triphenylphosphine with an alkyl halide, an alkenyl halide, a protected-hydroxyalkyl halide, and a protected hydroxyalkenyl halide. Alkenes prepared using this procedure may then be carried through to prepare a phosphine oxide in an analogous manner to that used to prepare phosphine oxide H in Scheme 1. Alternatively, an alkene analogous to compound C of Scheme 1 may be reduced with $(Ph_3P)_3RhCl$ and $H_2$ to provide other vitamin D analogs. See U.S. Pat. No. 5,945,410 and Sicinski, R. R. et al., *J. Med. Chem.*, 41, 4662-4674 (1998) both of which are hereby incorporated by reference in their entireties and for all purposes. Therefore, the procedure for forming the phosphine oxide shown in Scheme 1 may be used to prepare a wide variety of vitamin D analogs in addition to the compounds of the present invention.

Reference should be made to the following description as well as to Schemes 1, 2, and 3 for a detailed illustration of the preparation of compounds of formula 1A, 1B, and 1C and specifically 2-methylene-1α,25-dihydroxy-des-C,D-19-norvitamin $D_3$.

400 and 500 MHz using Bruker Instruments DMX-400 and DMX-500 Avance console spectrometers in $CDCl_3$. $^{13}C$ nuclear magnetic resonance (NMR) spectra were recorded at 125 MHz with a Bruker Instruments DMX-500 Avance console spectrometer in $CDCl_3$. Chemical shifts (δ) are reported downfield from internal $Me_4Si$ (δ0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

Schemes 1, 2, and 3 outline the synthetic procedures described below, in detail.

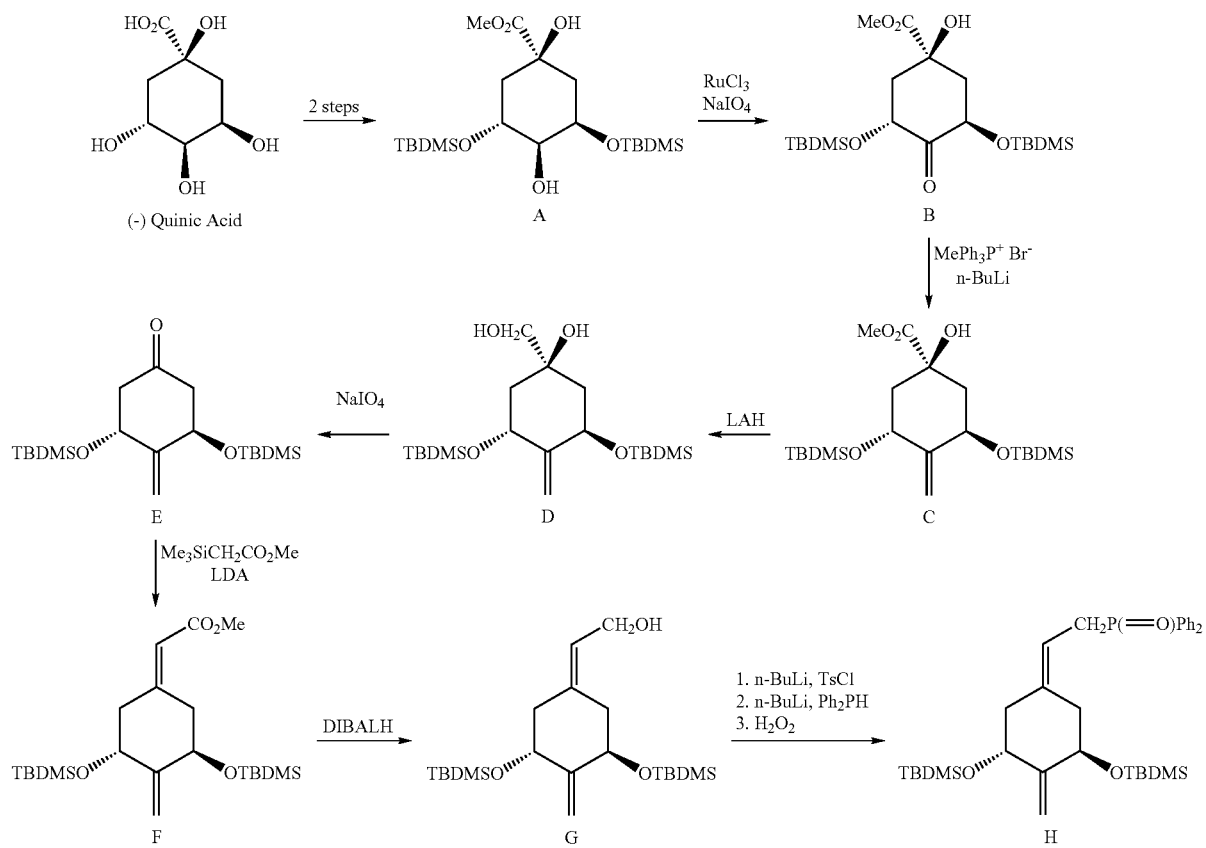

EXAMPLES

The synthesis and characteristics of various 19-nor vitamin D analogs is described in numerous United States patents including U.S. Pat. Nos. 5,843,928, 6,627,622, 6,579,861, 5,086,191, 5,585,369, and 6,537,981. Each of the above-described references is hereby incorporated by reference in its entirety and for all purposes as if fully set forth herein.

Melting points (uncorrected) were determined using a Thomas-Hoover capillary melting-point apparatus. Ultraviolet (UV) absorption spectra were recorded with a Perkin-Elmer Lambda 3B UV-VIS spectrophotometer in ethanol. $^1H$ nuclear magnetic resonance (NMR) spectra were recorded at Preparation of 2-Methylene-1α,25-Dihydroxy-des-C,D-19-norvitamin $D_3$ analog 19

A. Protection of 3-Hydroxy Group of Ester 1 (Scheme 2)

(2R)-3-Benzyloxymethoxy-2-methyl-propionic acid methyl ester (2)

To a solution of R-(−)-methyl-3-hydroxy-2-methylpropionate 1 (4 mL, 4.26 g, 0.036 mol) in anhydrous $CH_2Cl_2$ (30 mL) was added N,N-diisopropylethylamine (11.8 mL, 8.75 g, 0.06 mol) at room temperature. The mixture was cooled to −78° C. and benzyl chloromethyl ether (5.6 mL, 6.29 g, 0.04 mol) was added dropwise via cannula. The cooling bath was removed, and the reaction mixture was stirred at room temperature for 16 hours. Tetrabutylammonium iodide (50 mg) and benzyl chloromethyl ether (2 mL, 3.15 g, 0.02 mol) were then added to the reaction mixture. The mixture was stirred at room temperature for 3 hours, poured into water, and extracted with methylene chloride. The combined organic layers were dried over $Na_2SO_4$ and concentrated under reduced pressure. The residue was chromatographed on silica gel using hexane/EtOAc (9:1) as an eluent to give product 2 (8.29 g, 97%) as a colorless oil.

2: $[\alpha]^{24}_D$ –3° (c 0.17, $CHCl_3$); $^1$H NMR (500 MHz, $CDCl_3$) δ 1.19 (3H, d, J=7.1 Hz, CH—C$\underline{H}_3$), 2.77 (1H, m, C$\underline{H}$—$CH_3$), 3.64 (1H, dd, J=9.4, 5.4 Hz, one of C$\underline{H}_2$—CH), 3.70 (3H, s, $CH_3O$), 3.78 (1H, dd, J=9.4, 7.8 Hz, one of C$\underline{H}_2$—CH), 4.57 (2H, s, $OCH_2O$), 4.74 (2H, s, $CH_2Ph$), 7.29 (1H, m, Ar—$H_{para}$), 7.35 (4H, m, Ar—$H_{ortho,meta}$); $^{13}$C NMR (125 MHz) δ13.91 ($CH_3$), 39.99 ($\underline{C}H$—$CH_3$), 51.70 ($CH_3O$), 69.22 and 69.60 ($\underline{C}H_2CH$ and $CH_2Ph$), 94.50 ($OCH_2O$), 127.63, 127.84 and 128.33 ($Ar_{ortho,meta,para}$), 137.61 ($Ar_{ipso}$); MS (El) m/z (relative intensity) no $M^+$, 207($M^+$–$OCH_3$, 2), 131 (34), 120 (64), 91 (100); HRMS (ESI) exact mass calculated for $C_{13}H_{18}O_4Na$ ($M^+$+Na) 261.1103, measured 261.1110.

B. Reduction of Ester 2

(2R)-3-Benzyloxymethoxy-2-methyl-propan-1-ol (3)

A solution of ester 2 (0.5 g, 2.1 mmol) in anhydrous THF (4 mL) was added dropwise to a suspension of lithium aluminum hydride (0.16 g, 4.2 mmol) in anhydrous THF (10 mL) at 0° C. The cooling bath was removed, and the reaction was stirred at room temperature overnight, quenched with cold water, and extracted with EtOAc. The solvents were removed in vacuum and the crude oil was purified by silica gel chromatography using hexane/EtOAc (8:2) as an eluent to afford oily diol 3 (0.29 g, 66%).

3: $[\alpha]^{24}_D$ –3° (c 0.17, $CHCl_3$); ); $^1$H NMR (500 MHz, $CDCl_3$) δ0.92 (3H, d, J=7.1 Hz, CH—C$\underline{H}_3$), 2.02 (1H, m, C$\underline{H}$—$CH_3$), 2.39 (1H, s, OH), 3.54 (1H, dd, J=9.4, 7.6 Hz, one of C$\underline{H}_2$—CH), 3.60 (d, J=9.4 Hz, $CH_2OH$), 3.65 (1H, dd, J=9.4, 4.8 Hz, one of C$\underline{H}_2$—CH), 4.6 (2H, s, $OCH_2O$), 4.75 (2H, s, $CH_2Ph$), 7.30 (1H, m, Ar—$H_{para}$), 7.35 (4H, d, J=4.3 Hz, Ar—$H_{ortho,meta}$); $^{13}$C NMR (125 MHz) δ13.61 ($CH_3$), 35.62 ($\underline{C}H$—$CH_3$), 67.19 ($CH_2OH$), 69.58 ($\underline{C}H_2CH$), 72.38 ($CH_2Ph$), 94.79 ($OCH_2O$) 127.82, 127.90 and 128.49 ($Ar_{ortho,meta,para}$), 137.58 ($Ar_{ipso}$); MS (El) m/z (relative intensity) no $M^+$, 180 (8), 120(100), 108 (95), 89 (72); HRMS (ESI) exact mass calculated for $C_{12}H_{18}O_3Na$ ($M^+$+Na) 233.1154, measured 233.1158.

C. Tosylation of Hydroxy Compound 3

(R)-Toluene-4-sulfonic acid 3-benzyloxymethoxy-2-methyl-propyl ester (4)

To a mixture of diol 3 (29.2 mmol, 6.13 g), DMAP (0.82 mmol, 100 mg) and triethylamine (116.7 mmol, 16.2 mL, 11.8 g) in anhydrous $CH_2Cl_2$ (60 mL) was added tosyl chloride (37.9 mmol, 7.23 g) at 0° C. The reaction mixture was allowed to warm to room temperature and stirring was continued overnight. The mixture was then diluted with $CH_2Cl_2$ (100 mL) and was then washed with a saturated aqueous solution of $NaHCO_3$, dried over $Na_2SO_4$, and concentrated under reduced pressure. The residue was chromatographed on a silica gel using hexane/EtOAc (7:3) as an eluent to give the oily tosylate 4 (10.2 g, 97%).

4: $[\alpha]^{24}_D$ –5° (c 0.15, $CHCl_3$); $^1$H NMR (500 Hz, $CDCl_3$) δ0.94 (3H, d, J=7.1 Hz, CH—C$\underline{H}_3$), 2.09 (1H, m, C$\underline{H}$—$CH_3$), 2.42 (3H, s, $CH_3Ph$), 3.42 (1H, dd, J=9.4, 6.6 Hz, one of C$\underline{H}_2$—CH), 3.47 (1H, dd, J=9.4, 5.1 Hz, one of C$\underline{H}_2$—CH), 3.97 (1H, dd, J=9.4, 5.8 Hz, one of C$\underline{H}_2$-OTs), 4.03 (1H, dd, J=9.4, 5.8 Hz, one of C$\underline{H}_2$—OTs), 4.51 (2H, s, $OCH_2O$), 4.65 (2H, s, $CH_2Ph$), 7.30 (7H, br m, Ar—H), 7.78 (2H, J=8.2 Hz, Ar—$H_{ortho}$ from tosyl); $^{13}$C NMR (125 MHz) δ13.58 ($CH_3$), 21.60 (Ph—$CH_3$), 33.45 ($\underline{C}H$—$CH_3$), 68.61 ($\underline{C}H_2CH$), 69.27 ($CH_2OTs$), 71.96 ($CH_2Ph$), 94.56 ($OCH_2O$), 127.68, 127.82, 128.36, 129.75, 132.6, 137.58 and 144.66 (Ar); MS (El) m/z (relative intensity) no M+, 257($M^+$–$OCH_2Ph$, 65), 245 (55), 227 (81), 86 (100); HRMS (ESI) exact mass calculated for $C_{19}H_{24}O_5SNa$ ($M^+$+Na) 387.1242, measured 387.1252.

D. Reaction of Tosylate 4 with Grignard Reagent (S)-1-Benzyloxymethoxy-2,6-dimethyl-hept-5-ene (5)

4-Chloro-2-methyl-2-butane (15.5 mL, 14.4 g, 137.5 mmol) was added dropwise to stirred magnesium turnings (6.75 g, 225 mmol) in anhydrous THF (465 mL) under argon at 0° C. The stirring was continued 0° C. for 1 hour. The cooling bath was removed, and the mixture was stirred at room temperature for an additional 1.5 hours. The mixture was then cooled to –78° C. and the formed Grignard reagent was added via cannula to a solution of tosylate 4 (10 g, 27.5 mmol) in anhydrous THF (70 mL). $Li_2CuCl_4$ (160mL) [previously prepared from LiCl (1.36 g, 32.1 mmol) and $CuCl_2$ (2.17 g, 16.1 mmol)] was then added to the reaction mixture. The cooling bath was removed, and the reaction was stirred at room temperature for 17 hours. The mixture was extracted with $CH_2Cl_2$, and the organic layer was washed with $NH_4Cl$ and $NaHCO_3$, dried over $Na_2SO_4$, and evaporated. The residue was chromatographed on silica gel using hexane/EtOAc (7:3) as an eluent to give oily product 5 (5.65 g, 78%).

5: $[\alpha]^{24}_D$ +2° (c 0.24, $CHCl_3$); $^1$H NMR (400 Hz, $CDCl_3$) δ0.94 (3H, d, J=6.6 Hz, CH—C$\underline{H}_3$), 1.18 and 1.46 (1H and 1H, each m), 1.60 and 1.68 [3H and 3H, each s, =C($CH_3$)$_2$], 1.87 (1H, m, C$\underline{H}$—$CH_3$), 2.05 (2H, m, =$CCH_2$), 3.37 (1 H, dd, J=9.4, 6.8 Hz, one of C$\underline{H}_2$—CH), 3.44 (1H, dd, J=9.4, 5.8 Hz, one of C$\underline{H}$—CH), 4.60 (2H, s, $OCH_2O$), 4.76 (2H, s, $CH_2Ph$), 5.10 (1H, br t, J~7 Hz, CH=C), 7.30 (1H, m, Ar—$H_{para}$), 7.34 (4H, m, Ar—$H_{ortho,meta}$); $^{13}$C NMR (125 MHz) δ16.96 (CH—$\underline{C}H_3$), 17.53 (one of $\underline{C}H_3C$=), 25.60 (one of $\underline{C}H_3C$=), 32.92 ($\underline{C}H$—$CH_3$), 33.57 ($CH_2\underline{C}H_2CH$), 69.27 ($\underline{C}H_2$-Ph), 73.37 ($\underline{C}H_2CH$), 94.64 ($OCH_2O$), 124.49 ($\underline{C}$—$CH_3$), 127.52, 127.77, 128.28, ($Ar_{ortho,meta,para}$), 137.95 [=$\underline{C}(CH_3)_2$]; MS (El) m/z (relative intensity) 262 ($M^+$, 22), 232.2 (65), 154.1 (100); HRMS (ESI) exact mass calculated for $C_{17}H_{26}O_2Na$ ($M^+$+Na) 285.1830, measured 285.1837.

E. Epoxidation of Olefin 5

(2S)-1-Benzyloxymethoxy-2,6-dimethyl-5,6-epoxy-heptane (6)

Olefin 5 (3.2 g, 12.2 mmol) was dissolved in anhydrous $CH_2Cl_2$ (60 mL), and $NaHCO_3$ (1.6 g, 18.4 mmol) was added. Then, 3-chloroperoxybenzoic acid (60%, 12.8 g, 36.6 mmol) was added at room temperature with stirring. The stirring was continued for 24 hours, and the mixture was diluted with ether, and shaken with water and 2M NaOH. The organic layer was washed with water and saturated $NH_4Cl$, dried over $Na_2SO_4$, and evaporated. The residue was chromatographed on silica gel using hexane/EtOAc (9:1) as an eluent to give the oily product 6 (2.5 g, 74%).

6: $[\alpha]^{24}_D$ -1.7° (c 0.88, CHCl$_3$); $^1$H NMR (500 Hz, CDCl$_3$) δ0.96 (3H, d, J=6.7 Hz, CH—C$\underline{H}_3$), 1.25 (1H, m), 1.27 and 1.31 [3H and 3H, each s, C(CH$_3$)$_2$], 1.5-1.7 (3H, br m), 1.79 (1H, m, C$\underline{H}$—CH$_3$), 2.73 (1H, m, CH$_2$C$\underline{H}$O), 3.45 (2H, br m, C$\underline{H}_2$—CH), 4.60 (2H, s, OCH$_2$O), 4.76 (2H, s, CH$_2$Ph), 7.29 (1H, m, Ar—H$_{para}$), 7.34 (4H, d, J=4.3 Hz, Ar—H$_{ortho,meta}$).

F. Reduction of Epoxide 6

(S)-7-Benzyloxymethoxy-2,6-dimethyl-heptan-2-ol (7)

To a solution of the epoxide 6 (2.5 g, 9 mmol) in anhydrous ether (75 mL) at 0° C. was added lithium aluminum hydride (1.7 g, 67.5 mmol). The cooling bath was removed and the reaction was stirred at room temperature overnight. The reaction was then quenched with cold water and aqueous NH$_4$Cl, and extracted with CH$_2$Cl$_2$. The solvents were removed under reduced pressure and the crude oil was chromatographed on a silica gel using hexane/EtOAc (9:1) as an eluent to give an oily alcohol 7 (2 g, 80%).

7: $[\alpha]^{24}_D$ -4° (c 0.19, CHCl$_3$); $^1$H NMR (200 Hz, CDCl$_3$) δ0.94 (3H, d, J=6.5 Hz, CH—C$\underline{H}_3$), 1.20 [6H, s, (CH$_3$)$_2$COH], 1.75 (1H, m, C$\underline{H}$—CH$_3$), 3.38 (1H, d, J=10.8, 6.6 Hz, one of C$\underline{H}_2$—CH), 3.46 (1H, dd, J=10.8, 6.0 Hz, one of C$\underline{H}_2$—CH), 4.60 (2H, s, OCH$_2$O), 4.76 (2H, s, CH$_2$Ph), ca. 7.3 (5H, m, Ar—H); HRMS (ESI) exact mass calculated for C$_{17}$H$_{28}$O$_3$Na (M$^+$+Na) 303.1936, measured 303.1947.

G. Removal of BOM Protecting Group 2,6-Dimethyl-heptane-1,6-diol (8)

To a solution of an alcohol 7 (1.8 g, 0.01 mol) in ethyl acetate (20 mL) was added Pd/C (10%, 100 mg) at room temperature. The reaction mixture was stirred for 5 days and Pd/C (150 mg) was added 3 times per day. The reaction was then filtered, and the solvent was evaporated under reduced pressure. The crude oil was chromatographed on silica gel using hexane/EtOAc (1:1) as an eluent to give an oily diol 8 (0.95 g, 92%).

8: $[\alpha]^{24}_D$+11° (c 1.28, CHCl$_3$); $^1$H NMR (200 Hz, CDCl$_3$) δ0.93 (3H, d, J=6.6 Hz, CH—C$\underline{H}_3$), 1.20 [6H, s, (CH$_3$)$_2$COH], 1.65 (1H, m, C$\underline{H}$—CH$_3$), 3.45 (2H, br m, C$\underline{H}_2$—CH); $^{13}$C NMR (50 MHz) δ16.63 (CH—C$\underline{H}_3$), 21.64 (CH$_2$—CH$_2$—CH$_2$), 29.19 [C(C$\underline{H}_3$)], 29.29 [C(C$\underline{H}_3$)], 33.62 (CH—C$\underline{H}_2$—CH$_2$), 35.68 (C$\underline{H}$—CH$_3$), 44.03 (C$\underline{H}_2$COH), 68.19 (CH$_2$OH), 71.16 [$\underline{C}$(CH$_3$)$_2$]; MS (ES) 183 (M$^+$+Na); HRMS (ESI) exact mass calculated for C$_9$H$_{20}$O$_2$Na (M$^+$+Na) 183.1361, measured 183.1351.

H. Oxidation of Diol 8

(S)-6-Hydroxy-2,6-dimethyl-heptanal (9)

Pyridinium dichromate (1.5 g, 3.75 mmol) was added to a stirred solution of diol 8 (110 mg, 0.69 mmol) and pyridinium p-toluenesulfonate (33 mg, 0.11 mmol) in CH$_2$Cl$_2$ (5 mL). The resulting suspension was stirred for 4 hours at room temperature under argon. The reaction was then filtered through Celite and solvent was evaporated under reduced pressure. The residue was chromatographed on silica gel using hexane/EtOAc (9:1) as an eluent to give an oily aldehyde 9 (65 mg, 60%).

9: $[\alpha]^{24}_D$ -10.5° (c 1.1, CHCl$_3$); $^1$H NMR (400 Hz, CDCl$_3$) δ1.06 (3H, d, J=7.0 Hz, CH—C$\underline{H}_3$), 1.21 [6H, s, (CH$_3$)$_2$COH], 2.37 (1H, m, C$\underline{H}$—CH$_3$), 9.62 (1 H, d, J=1.9 Hz, CHO); $^{13}$C NMR (25 MHz) δ13.33 (CH—C$\underline{H}_3$), 21.70 (CH$_2$—C$\underline{H}_2$—CH$_2$), 29.21 [C(C$\underline{H}_3$)$_2$], 30.89 (CH—C$\underline{H}_2$), 43.70 (C$\underline{H}_2$COH), 46.30 (C$\underline{H}$CH$_3$), 71.16 [$\underline{C}$(CH$_3$)$_2$], 205.25 (CHO).

I. Silylation of Hydroxy Aldehyde 9

(S)-2,6-Dimethyl-6-triethylsilanyloxy-heptanal (10)

To a solution of aldehyde 9 (93.4 mg, 0.6 mmol) and 2,6-lutidine (170 μL, 1.5 mmol) in anhydrous CH$_2$Cl$_2$ (3.7 mL) was added dropwise Et$_3$SiOTf (161 μL, 0.72 mmol) at 0° C. under argon. The solution was stirred at 10° C. for 3 hours and then at room temperature for 30 minutes. The mixture was quenched with cold water and extracted with CH$_2$Cl$_2$. The solvent was removed under reduced pressure, and the residue was chromatographed on silica Sep-Pak cartridge using hexane/EtOAc (99.7:0.3) as an eluent to give an oily aldehyde 10 (130 mg, 81%).

10: $[\alpha]^{24}_D$+4.2° (c 1.75, CHCl$_3$); $^1$H NMR (500 Hz, CDCl$_3$) δ0.56 (6H, q, J=7.8 Hz, 3×SiCH$_2$), 0.94 (9H, t, J=7.8 Hz, 3×SiCH$_2$C$\underline{H}_3$), 1.10 (3H, d, J=6.8 Hz, CH—C$\underline{H}_3$), 1.19 [6H, s, (CH$_3$)$_2$CO], 2.37 (1H, d sext, J=1.9, 6.8 Hz, CH—CHO), 9.62 (1H, d, J=1.95 Hz, CHO).

J. Wittig Reaction of Aledhyde 10

(Z)-(S)-1-(t-Butyl-dimethyl-silanyloxy)-5,9-dimethyl-9-triethylsilanyloxy-dec-3-ene (12)

To a solution of a phosphonium bromide 11 (275 mg, 0.54 mmol) in anhydrous THF (12 mL) was added dropwise n-BuLi (2 M in cyclohexane, 270 μL, 0.54 mmol) at −20° C. After 15 minutes of stirring at −20° C., the reaction was cooled to −50° C. and ⅔ of the orange solution of the formed Wittig reagent was added via cannula to the stirred solution of aldehyde 10 (50 mg, 0.18 mmol) in anhydrous THF (2 mL). After 1 hour of stirring at −50° C., brine and 1 M HCl were added, and the mixture was extracted with EtOAc. The organic layer was washed with water and evaporated. The residue was chromatographed on silica Sep-Pak cartridge eluted with hexane/EtOAc (98.5:1.5) to give an oily compound 12 (59.3 mg, 75%).

12: $[\alpha]^{24}_D$ -5.5° (c 0.48, CHCl$_3$); $^1$H NMR (500 Hz, CDCl$_3$) δ0.058(6H, s, 2×CH$_3$Si), 0.55 (6H, q, J=7.8 Hz, 3×SiCH$_2$), 0.89 [9H, s, (C$\underline{H}_3$)$_3$C], 0.93(3H, d, J=6.8 Hz, C$\underline{H}_3$CH), 0.94 (9H, t, J=7.8 Hz, 3×SiCH$_2$C$\underline{H}_3$), 2.27 (2H, m, C$\underline{H}_2$CH=), 2.42 (1H, m, C$\underline{H}$—CH$_3$), 3.59 (2H, m, OCH$_2$), 5.20 (dd, J=10.8, 9.7 Hz, =C$\underline{H}$—CHCH$_3$), 5.29 (1H, dt, J=10.8, 7.4 Hz, CH$_2$C$\underline{H}$=CH); $^{13}$C NMR (125 MHz) δ−5.28 [SiCH$_3$], 6.75 (SiCH$_2$), 7.10 (C$\underline{H}_3$CH$_2$Si), 18.37 [Si$\underline{C}$(CH$_3$)$_3$], 21.29 [SiC(C$\underline{H}_3$)$_3$], 22.32(CH$_2$—CH$_2$—CH$_2$), 25.95 (CH—C$\underline{H}_3$), 29.80 and 29.89 [C(C$\underline{H}_3$)$_2$], 31.41 (C$\underline{H}_2$CH=), 31.90 (C$\underline{H}$—CH$_3$), 38.06 (CH—C$\underline{H}_2$—CH$_2$), 45.20 (C$\underline{H}_2$CO), 63.23 (CH$_2$O), 73.23 [$\underline{C}$(CH$_3$)$_2$], 123.82 (CH$_2$—C$\underline{H}$=), 138.34 (=C$\underline{H}$CH); MS (ES) 451 (M$^+$+Na); HRMS (ES) exact mass calculated for C$_{24}$H$_{52}$O$_2$Si$_2$Na (M$^+$+Na) 451.3404, measured 451.3414.

K. Hydrolysis of Silyl Protecting Groups in Diether 12 (Scheme 3)

(3Z)-(5S)-5,9-Dimethyl-dec-3-ene-1,9-diol (13)

To a stirred solution of compound 12 (201 mg, 0.4 mmol) in anhydrous CH$_2$Cl$_2$ (10 mL) was added hydrofluoric acid (48%, 6 mL). After 40 minutes of stirring at room temperature, water was added, and the organic layer was separated, washed with water and NaHCO$_3$, dried over MgSO$_4$, and evaporated. The residue was chromatographed on silica Sep-Pak cartridge using hexane/EtOAc (6:4) as an eluent to give an oily diol 13 (76.4 mg, 92%).

13: $^1$H NMR (500 Hz, CDCl$_3$) δ0.95 (3H, d, J=6.7 Hz, CH$_3$CH), 1.19 and 1.20 [3H and 3H, each s, C(CH$_3$)$_2$], 2.33 (2H, m, CH$_2$CH=), 2.48 (1H, br m, CH—CH$_3$), 3.64 (2H, t, J=6.4 Hz, CH$_2$OH), 5.31 (2H, m, CH=CH); $^{13}$C NMR (50 MHz) δ21.63 (CH—CH$_3$), 22.26 (CH$_2$—CH$_2$—CH$_2$), 29.25 and 29.60 [C(CH$_3$)$_3$], 31.27 (CH$_2$CH=), 31.87 (CH—CH$_3$), 37.96 (CH—CH$_2$—CH$_2$), 44.00 (CH$_2$CO), 62.55 (CH$_2$OH), 71.29 [C(CH$_3$)$_2$], 124.09 (CH$_2$—CH=), 139.70 (=CHCH).

L. Hydrogenation of Unsaturated Diol 13

(5R)-5,9-Dimethyl-decane-1,9-diol (14)

To a solution of diol 13 (55 mg, 0.27 mmol) in ethyl acetate (10 mL) was added Pd/C (10%, 50 mg). The reaction mixture was stirred for 18 hours under a continuous stream of hydrogen at room temperature. The mixture was then filtered, and the solvent was evaporated under reduced pressure. The crude oily product was chromatographed on silica Sep-Pak cartridge eluted with hexane/EtOAc (8:2) to give an oily diol 14 (55 mg, 45%).

14: $[\alpha]^{24}_D$-5.9° (c 0.27, CHCl$_3$), $^1$H NMR (200 Hz, CDCl$_3$) δ0.87 (3H, d, J=6.4 Hz, CH—CH$_3$), 1.21 [6H, s, C(CH$_3$)$_2$], 1.56 (1H, br m, CH—CH$_3$), 3.64(2H, t, j=6.4 Hz, CH$_2$OH); $^{13}$C NMR (50 MHz) δ19.61 (CH—H$_3$), 21.75 (CH$_2$), 23.22 (CH$_2$), 29.24 and 29.29 [C(CH$_3$)], 32.75 (CH—CH$_3$), 33.10 (CH$_2$), 36.76 (CH$_2$), 37.48(CH$_2$), 44.22 (CH$_2$CO), 63.07 (CH$_2$OH), 71.11 [C(CH3)2]; MS (ES) 225 (M$^+$+Na); HRMS (ES) exact mass calculated for C$_{12}$H$_{24}$O$_2$Na (M$^+$+Na) 225.1831, measured 225.1823.

M. Oxidation of Diol 14

9-Hydroxy-5,9-dimethyl-decanal (15)

To a stirred solution of diol 14 (25 mg, 0.12 mmol) in anhydrous CH$_2$Cl$_2$ (3.5 mL) was added Dess-Martin reagent (73 mg, 0.15 mmol) at room temperature. The reaction was stirred at room temperature for 1.5 hours. Then, an aqueous solution of sodium thiosulfate (6 mL) and saturated NaHCO$_3$ (6 mL) were added. The reaction was extracted with CH$_2$Cl$_2$, solvents were removed under reduced pressure, and the crude oil was purified on silica Sep-Pak using hexane/EtOAc (7:3) as an eluent to give an oily aldehyde 15 (16.5 mg, 67%).

15: $^1$H NMR (200 Hz, CDCl$_3$) δ0.88 (3H, d, J=6.4 Hz, CH—CH$_3$), 1.21 [6H, s, C(CH$_3$)$_2$], 2.41 (2H, dt, J=1.7, 7.3 Hz, CHCHO), 9.77 (1H, t, J=1.7 Hz, CHO).

N. Silylation of Hydroxy Aldehyde 15

5,9-Dimethyl-9-triethylsilanyloxy-decanal (16)

To a solution of aldehyde 15 (16.5 mg, 82.5 µmol) and 2,6-lutidine (24 µL, 206 ,µmol) in anhydrous CH$_2$Cl$_2$ (1.1 mL) was added dropwise Et$_3$SiOTf (42 µL, 165 µmol) at -78° C. The mixture was stirred for 2 hours at -78° C. and for one additional hour at -50° C. Water and CH$_2$Cl$_2$ were added, the organic layer was washed with water, dried over MgSO$_4$, and evaporated. The residue was chromatographed on silica Sep-Pak cartridge using hexane/EtOAc (99.7:0.3) as an eluent to give oily aldehyde 16 (22 mg, 85%). An analytical sample was obtained using HPLC (10 mm ×25 cm Zorbax-Sil column, 4 mL/min) with a hexane/EtOAc (98:2) solvent system. Analytically pure aldehyde 16 was collected at Rv=33 mL.

16: $^1$H NMR (500 Hz, CDCl$_3$) δ0.55 (6H, q, J=7.9 Hz, 3×SiCH$_2$CH$_3$), 0.88 (3H, d, J=6.4 Hz, CH—CH$_3$), 0.94 (9H, t, J=7.9 Hz, 3×SiCH$_2$CH$_3$), 1.19 [6H, s, C(CH$_3$)$_2$], 2.41 (2H, m, CH$_2$CHO), 9.77 (1H, t, J=1.8 Hz, CHO).

O. Wittig-Horner Reaction of Aldehyde 16

(1R,3R,7'R)-1, 3-Bis-(tert-butyl-dimethyl-silanoxy)-5-(7 ',1 '-dimethyl-11'-triethylsilanyloxy-dodec-2'-enylidene)-2-methylene-cyclohexane (18)

To a solution of phosphine oxide 17 (45.7 mg, 78.5 µmol) in anhydrous THF (0.6 mL) at -78° C. was slowly added n-BuLi (51 µL, 81.8 µmol) under argon with stirring. The solution turned deep orange upon addition. The stirring was continued for 20 minutes at -78° C. and then a precooled solution of aldehyde 16 (22 mg, 70 µmol) in anhydrous THF (100 µL) was slowly added. The mixture was stirred for 3 hours at -78° C. and at 6° C. for 16 hours. EtOAc, saturated NaHCO$_3$ and brine were then added to the reaction vessel. The organic layer was washed with water, dried, and evaporated under reduced pressure. The residue was dissolved in hexane and applied on silica Sep-Pak cartridge using hexane/EtOAc (99.8:0.2) as an eluent to give the crude protected vitamin 18. The product was then purified by HPLC (10 mm × 25 cm Zorbax-Sil column, 4 mL/min) using a hexane/EtOAc (99.9:0.1) solvent system. Analytically pure vitamin D compound 18 (21.2 mg, 45%) was collected at Rv=18 mL.

18: UV (hexane) $\lambda_{max}$ 235.0 (ε 15 900), 242.0 (ε 24 800), 250.0 (ε 22 600) nm; $^1$H NMR (500 Hz, CDCl$_3$) δ0.04, 0.05, 0.07 and 0.08 (each 3H, each s, 4×SiCH$_3$), 0.57 (6H, q, J=7.9 Hz, 3×SiCH2CH$_3$), 0.86 (3H, d, J=7.4 Hz, CH—CH$_3$), 0.87 and 0.90 [9H and 9H, each s, 2×(CH$_3$)$_3$CSi], 0.95 (9H, t, J=7.9 Hz, 3×SiCH$_2$CH$_3$), 1.19 [6H, s, C(CH$_3$)$_2$], 2.07 (2H, m, 4'-H$_2$), 2.15 (1H, dd, J=12.5, 8.1 Hz), 2.35-2.5 (3H, br m), 4.43 (2H, m, 1- and 3-H), 4.94 and 4.95 (1 H and 1 H, each s, C=CH$_2$); 5.63 (1H, dt, J=15.0, 6.9 Hz, 3'-H), 5.90 (1H, d, J=10.9 Hz, 1'-H), 6.24 (1H, dd, J=15.0, 10.9 Hz, 2'-H); MS (EI) m/z (relative intensity) 678 (M+, 10), 649 (M$^+$–Et, 5), 621 (M$^+$–tBu, 12), 546 (12), 73 (100); HRMS (ESI) exact mass calculated for C$_{39}$H$_{78}$O$_3$Si$_3$ 678.5259, measured 678.5272.

P. Removal of Protecting Groups of 18

(1R,3R,7'R)-5-(1-Hydroxy-7,11-dimethyl-dodec-2-enylidene)-2-methylene-cyclohexane-1,3-diol (19)

To a stirred solution of 18 (21.2 mg, 31.2 µmol) in anhydrous THF (3 mL) was added tetrabutylammonium fluoride (1 M in THF, 370 µL, 0.37 mmol). The resulting mixture was stirred for 18 hours at room temperature. Solvent was removed in vacuo, and the residue was dissolved in hexane/EtOAc (9:1) and applied on silica Sep-Pak. Elution with hexane/EtOAc (1:1) provided crude product 19. The vitamin was further purified by HPLC (10 mm ×25 cm Zorbax-Sil column, 4 mL/min) using a hexane/2-propanol (8:2) solvent system. Analytically pure vitamin D compound 19 (6.9 mg, 66%) was collected at Rv=21 mL.

19: UV (hexane) $\lambda_{max}$ 234.0 (ε27 800), 241.0 (ε30 200), 248.5 (sh, ε19 900) nm; $^1$HNMR (400 Hz, CDCl$_3$) δ0.86 (3H, d, J=6.5 Hz, CH—CH$_3$), 1.21 [6H, s, C(CH$_3$)$_2$], 2.08 (2H, q, J=6.9 Hz, 4'-H$_2$), 2.26 (1H, dd, J=13.1, 7.1 Hz), 2.39(1H, dd, J=13.4, 7.2 Hz), 2.56 (1H, dd, J=13.5, 4.2 Hz), 2.70 (1H, dd, J=13.3, 4.3 Hz), 4.48 (2H, m, 1- and 3-H), 5.10 (2H, s, C=CH$_2$); 5.70 (1H, dt, J=15.0, 6.9 Hz, 3'-H 6.03 (1H, d, J=10.8 Hz, 1'-H), 6.29 (1H, dd, J=15.0, 10.8 Hz, 2'-H); MS (EI) m/z (relative intensity) no M$^+$, 318 (M$^+$–H$_2$O, 19), 300 (8), 285 (4), 59 (100); HRMS (ESI) exact mass calculated for C$_{21}$H$_{34}$O$_2$ (M$^+$–H$_2$O) 318.2559, measured 318.2570.

Scheme 2
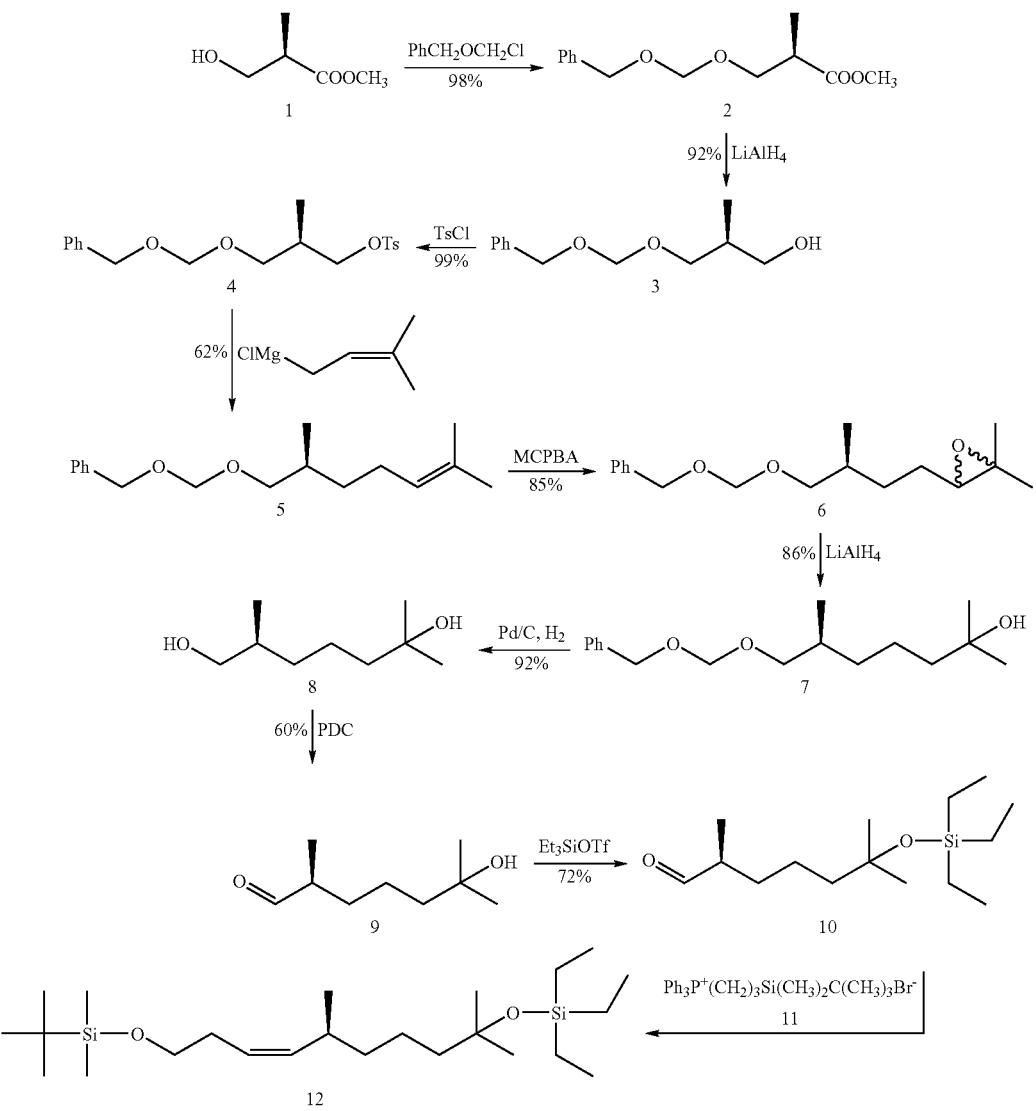
Scheme 3
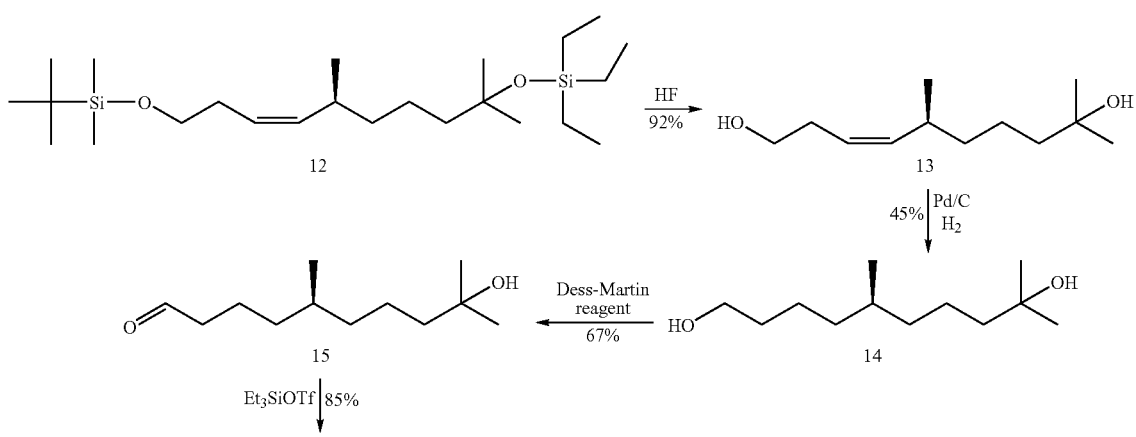

-continued

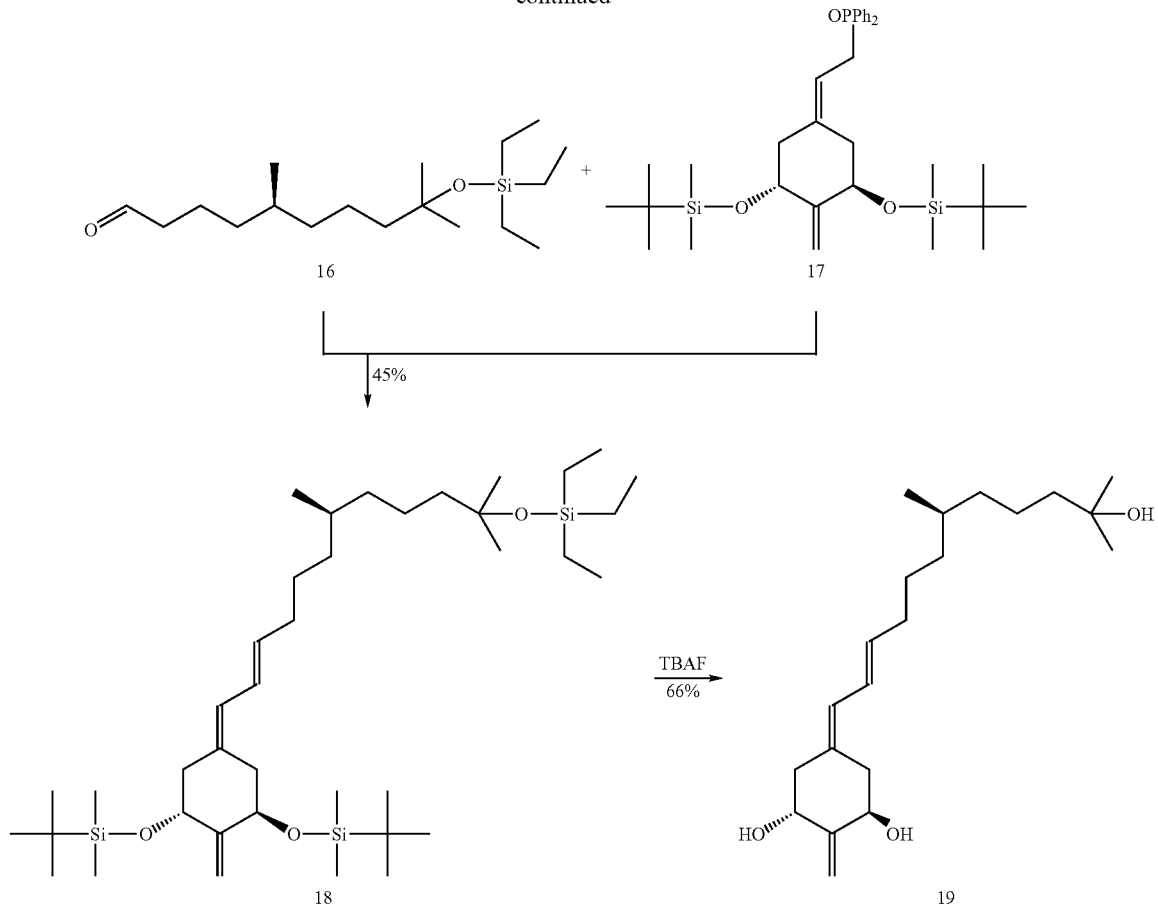

BIOLOGICAL ACTIVITY

Vitamin D Receptor Binding

Test Material

Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand is bound to the receptor.

Study Druqs

Unlabeled ligands were dissolved in ethanol and the concentrations were determined using UV spectrophotometry ($1,25(OH)_2D_3$: molar extinction coefficient=18,200 and $\lambda_{max}$=265 nm). Radiolabeled ligand ($^3H$-$1,25(OH)_2D_3$, ~159 Ci/mmol) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and was mixed at 10-minute intervals for 30 minutes. The hydroxylapatite was collected by centrifugation and was then washed three times with Tris-EDTA buffer (50 mM Tris, 1.5 mM EDTA, pH 7.4) containing 0.5% Titron X-100. After the final wash, the pellets were transferred to scintillation vials containing 4 mL of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations was tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/mL. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contain intracellular black-blue formazan deposits. Verification of differentiation to monocytic cells was determined by measuring phagocytic activity.

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Antagonism was tested by adding a combination of 1,25 $(OH)_2D_3$ and the compound in the same well keeping the final ethanol concentration the same.

Intestinal Calcium Transport and Bone Calcium Mobilization

Male, weanling Sprague-Dawley rats were placed on Diet 11 (Suda et al. J. Nutr. 100:1049, 1970) (0.47% Ca) diet+ vitamins AEK for one week followed by Diet 11 (0.02% Ca) +AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium was determined as a measure of bone calcium mobilization. The first 10 cm of the intestine was also collected for intestinal calcium transport analysis using the everted gut sac method. Antagonism was tested by administering a combination of $1,25(OH)_2D_3$ and the compound to the animal simultaneously.

The compounds of the invention were prepared and studied using the methods described above. The compounds were/are found to exhibit desired, and highly advantageous, patterns of biological activity with respect to intestinal calcium transport activity, ability to mobilize calcium from bone, and ability to bind to the vitamin D receptor. The compounds are also found to moderate cell differentiation activity.

Figure 2:
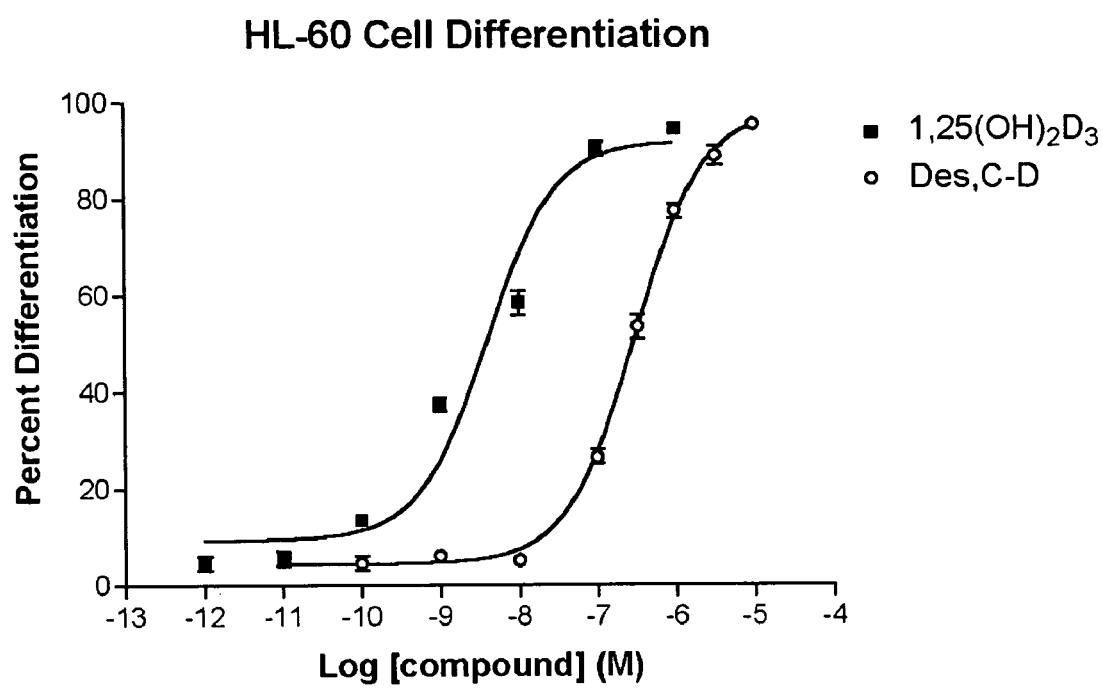
Figure 3:
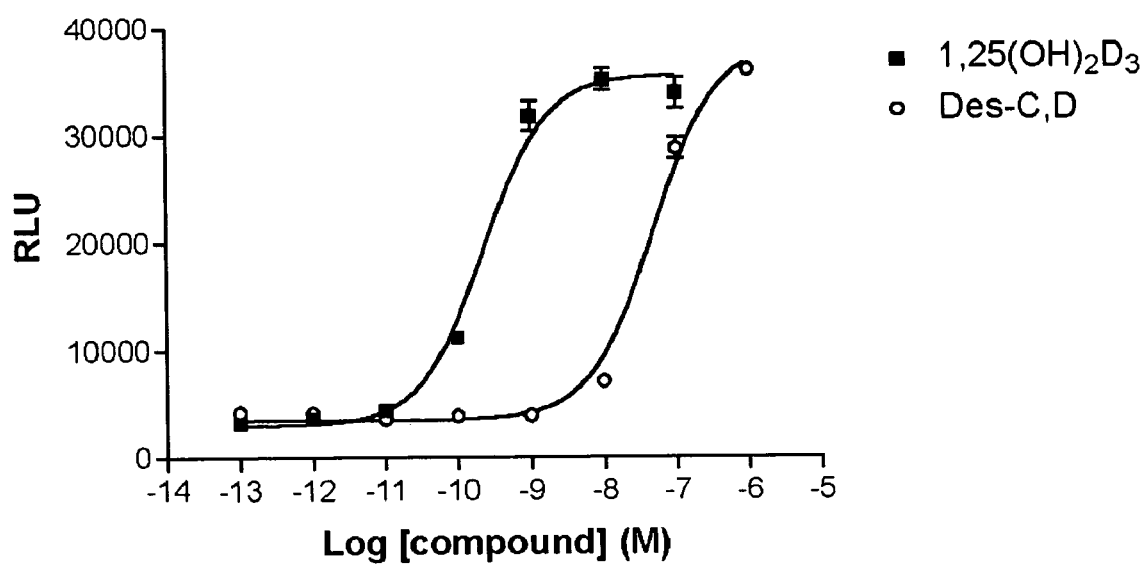
Figure 4:
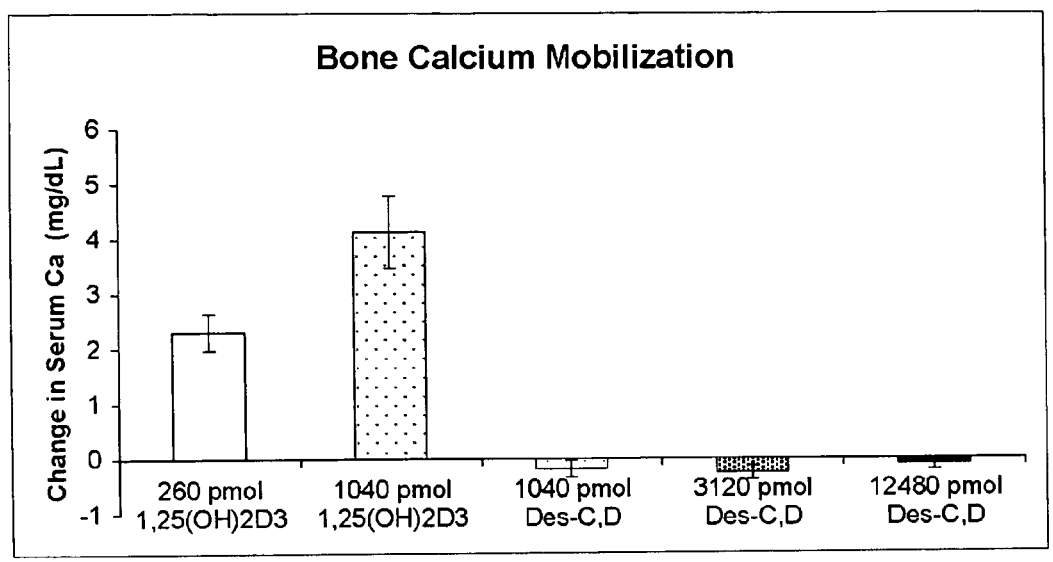

The compound of formula 1C4 (Des-C,D) does not bind to the vitamin D receptor as strongly as the native hormone 1,25-$(OH)_2D_3$ as shown in FIG. 1. Des-C,D does not show as much activity as 1,25-$(OH)_2D_3$ in inducing differentiation of HL-60 cells (FIG. 2). Des C,D also does not show as much activity in causing transcription as 1,25-$(OH)_2D_3$ in this respect as shown in FIG. 3. Finally, as shown in FIG. 4, Des C,D has no measureable bone calcium mobilizing activity even at the very high dose of 12,480 pmol/day.

For treatment purposes, the compounds of the invention may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, anti-oxidants, binders, coloring agents or emulsifying or taste-modifying agents. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is hereby incorporated by reference in its entirety and for all purposes as if fully set forth herein.

The compounds may be administered orally, topically, parenterally, rectally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from 0.001 µg to about 1 mg per day of the compound are appropriate for treatment purposes. In some such embodiments an appropriate and effective dose may range from 0.01 µg to 1 mg per day of the compound. In other such embodiments an appropriate and effective dose may range from 0.1 µg to 500 µg per day of the compound. Such doses will be adjusted according to the type of disease or condition to be treated, the severity of the disease or condition, and the response of the subject as is well understood in the art. The compound may be suitably administered alone, or together with another active vitamin D compound.

Compositions for use in the invention include an effective amount of a compound of any of the embodiments as the active ingredient or ingredients, and a suitable carrier. An effective amount of the compound or compounds for use in accordance with some embodiments of the invention will generally be a dosage amount such as those described herein, and may be administered topically, transdermally, orally, nasally, rectally, or parenterally.

Dosages as described above are suitable, it being understood that the amounts given are to be adjusted in accordance with the severity of the disease, and the condition and response of the subject as is well understood in the art. As noted, the compounds of the invention may be present as a mixture of two or more compounds. In some mixtures, the mixture may include a first compound of the invention and a second compound of the invention. In some embodiments, the mixture includes the first compound and the second compound, and the ratio of the first compound to the second compound ranges from 50:50 to 99.9:0.1. In some such embodiments, the ratio of the first compound to the second compound ranges from 70:30 to 99.9:0.1, from 80:20 to 99.9:0.1, from 90:10 to 99.9:0.1, or from 95:5 to 99.9:0.1.

The compound or compounds may be formulated as creams, lotions, ointments, aerosols, suppositories, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, anti-oxidants, emulsifiers, coloring agents, binders or taste-modifying agents.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100 microns.

The formulations may conveniently be presented in dosage unit form and may be prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

All references cited herein are specifically incorporated by reference in their entireties and for all purposes as if fully set forth herein.

It is understood that the invention is not limited to the embodiments set forth herein for illustration, but embraces all such forms thereof as come within the scope of the following claims.

What is claimed is:

1. A compound of formula 1:

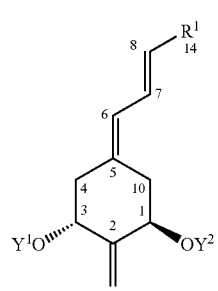

wherein,
$R^1$ is a straight or branched chain alkyl or alkylene group having from 8 to 27 carbons and bearing an $OY^3$ group; and
$Y^1$, $Y^2$ and $Y^3$ are independently selected from H or hydroxy-protecting group.

2. The compound of claim 1, wherein the compound has the formula 1A, 1B, or 1C

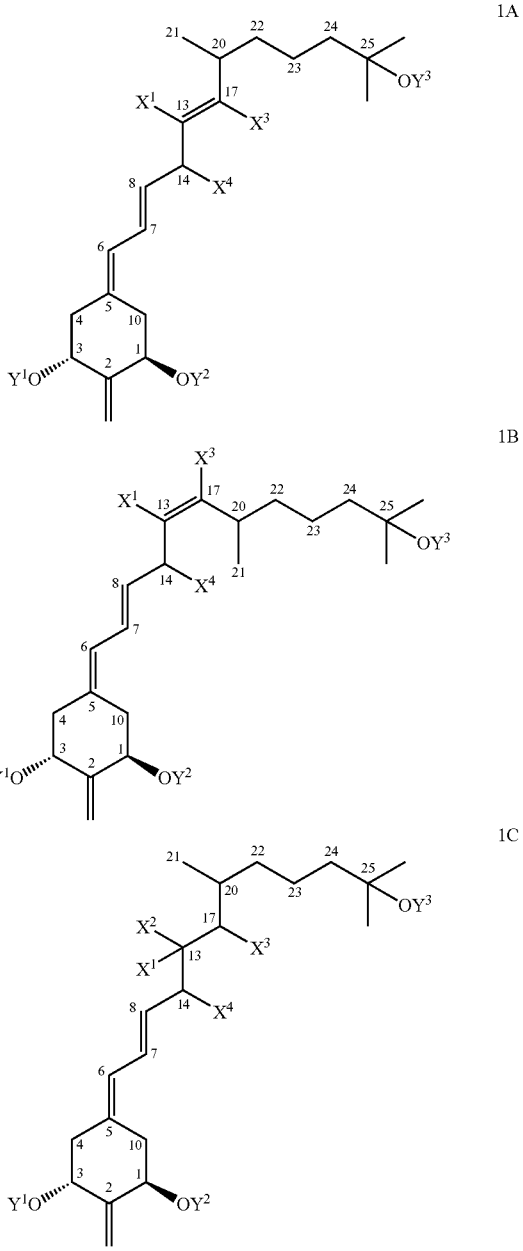

wherein,
$X^1$, $x^2$, $X^3$, and $X^4$ are independently selected from H or straight or branched chain alkyl groups having from 1 to 4 carbon atoms;
$Y^1$, $Y^2$, and $Y^3$ are independently selected from H or hydroxy-protecting groups;
the carbon atoms at positions 14 and 20 may independently have either the R or S configuration in the compound of formula 1A and formula 1B; and
the carbon atoms at positions 13, 14, 17, and 20 may independently have either the R or S configuration in the compound of formula 1C.

3. The compound of claim 2, wherein $Y^1$, $Y^2$, and $Y^3$ are all H and the compound has the formula 1A1, 1B1, or 1C1

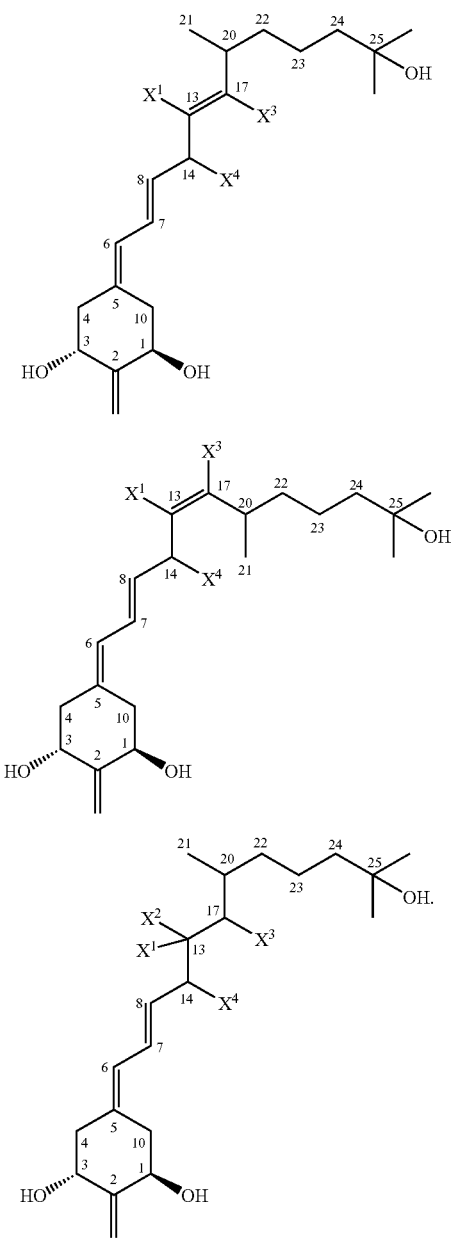

4. The compound of claim 2, wherein the compound has the formula 1A2, 1B2, or 1C2.

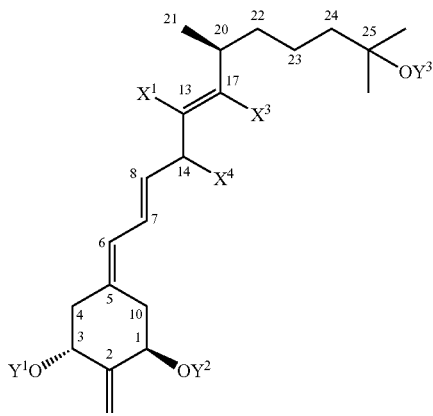

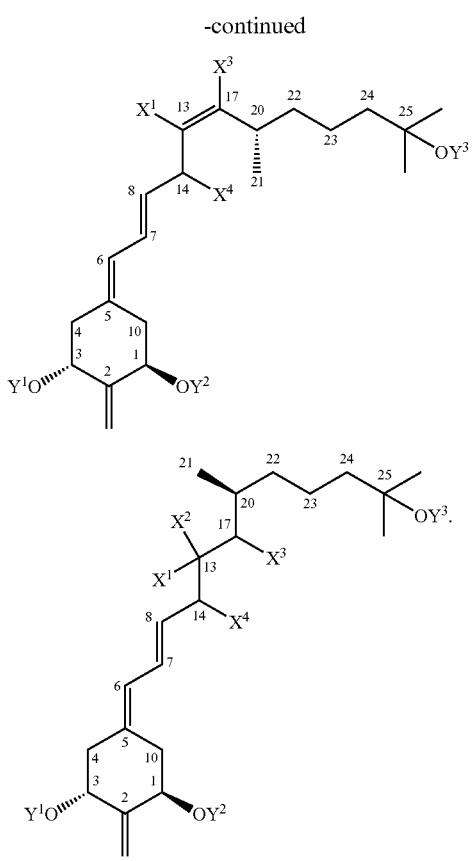

5. The compound of claim 2, wherein $X^1$, $X^2$, $X^3$, and $X^4$ are independently selected from H or methyl groups.

6. The compound of claim 5, wherein $X^1$, $X^2$, $X^3$, and $X^4$ are all H.

7. The compound of claim 2, wherein the compound has the formula 1C3

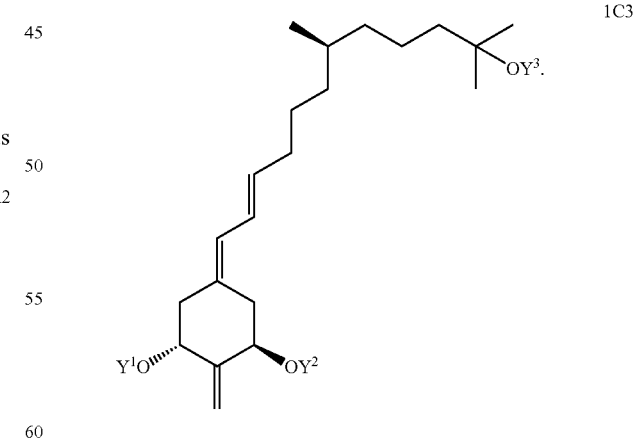

8. The compound of claim 1, wherein $Y^1$ and $Y^2$ are both hydroxy protecting groups.

9. The compound of claim 8, wherein $Y^1$ and $Y^2$ are both t-butyldimethylsilyl groups.

10. The compound of claim 1, wherein $Y^3$ is a trialkylsilyl group.

11. The compound of claim 10, wherein $Y^3$ is a triethylsilyl group.

12. The compound of claim 2, wherein the compound has the formula 1C4

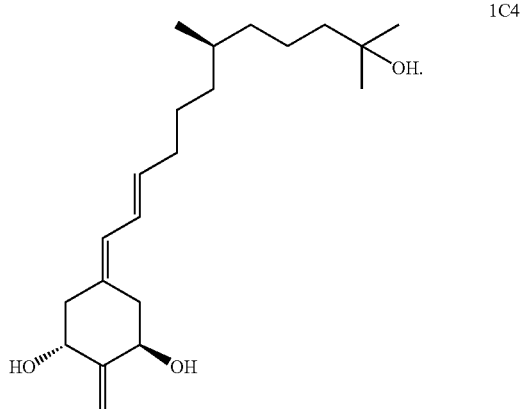

13. A pharmaceutical formulation, comprising: the compound of claim 1 and a pharmaceutically acceptable carrier.

14. The pharmaceutical formulation of claim 13, wherein the amount of the compound in the pharmaceutical formulation ranges from about 0.01 µg to about 1 mg per gram of the pharmaceutical formulation.

15. The pharmaceutical formulation of claim 13, wherein the amount of the compound in the pharmaceutical formulation ranges from about 0.1 µg to about 500 µg per gram of the pharmaceutical formulation.

16. A method of treating a subject suffering from a biological disorder, comprising administering an effective amount of the compound of claim 1, wherein the biological condition is selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, eczema, or inflammatory bowel diseases; a skin condition selected from wrinkles, lack of adequate skin firmness, lack of adequate dermal hydration, or insufficient sebum secretion; or secondary hyperparathyroidism.

17. The method of claim 16, wherein the compound is administered orally, parenterally, rectally, transdermally, or topically to the subject.

18. The method of claim 16, wherein the compound is administered by delivering the compound in an aerosol.

* * * * *